United States Patent
Bomati et al.

(10) Patent No.: US 10,344,269 B2
(45) Date of Patent: Jul. 9, 2019

(54) RECOMBINASE MUTANTS

(71) Applicant: Illumina Cambridge Limited, Nr Saffron Walden (GB)

(72) Inventors: Erin Bomati, San Diego, CA (US); Matthew William Kellinger, San Diego, CA (US); Jonathan Mark Boutell, Nr Saffron Walden (GB)

(73) Assignee: ILLUMINA CAMBRIDGE LIMITED, Essex (GB)

( * ) Notice: Subject to any disclaimer, the term of this patent is extended or adjusted under 35 U.S.C. 154(b) by 0 days.

(21) Appl. No.: 15/977,389

(22) Filed: May 11, 2018

(65) Prior Publication Data

US 2018/0258409 A1    Sep. 13, 2018

Related U.S. Application Data

(62) Division of application No. 14/869,744, filed on Sep. 29, 2015, now Pat. No. 9,982,244.

(60) Provisional application No. 62/057,056, filed on Sep. 29, 2014.

(51) Int. Cl.
  *C12N 9/14*    (2006.01)
  *C12Q 1/6844*  (2018.01)

(52) U.S. Cl.
  CPC ............. *C12N 9/14* (2013.01); *C12Q 1/6844* (2013.01); *C12Y 306/01008* (2013.01)

(58) Field of Classification Search
  CPC .. C12N 9/14; C12Q 1/6844; C12Q 2521/501; C12Y 306/01008
  See application file for complete search history.

(56) References Cited

U.S. PATENT DOCUMENTS

| | | |
|---|---|---|
| 5,223,414 A | 6/1993 | Zarling et al. |
| 7,270,981 B2 | 9/2007 | Armes et al. |
| 7,399,590 B2 | 7/2008 | Piepenburg et al. |
| 7,435,561 B2 | 10/2008 | Piepenburg et al. |
| 7,485,428 B2 | 2/2009 | Armes et al. |
| 7,666,598 B2 | 2/2010 | Piepenburg et al. |
| 7,742,463 B2 | 6/2010 | Lam et al. |
| 7,763,427 B2 | 7/2010 | Piepenburg et al. |
| 8,017,399 B2 | 9/2011 | Jarvis et al. |
| 8,030,000 B2 | 10/2011 | Piepenburg et al. |
| 8,062,850 B2 | 11/2011 | Piepenburg et al. |
| 8,071,308 B2 | 12/2011 | Piepenburg et al. |
| 8,563,748 B2 | 10/2013 | Korte et al. |
| 8,637,253 B2 | 1/2014 | Piepenburg et al. |
| 2013/0338042 A1 | 12/2013 | Shen et al. |
| 2016/0326502 A1 | 11/2016 | Piepenburg et al. |

FOREIGN PATENT DOCUMENTS

| | | |
|---|---|---|
| WO | WO 2008/035205 | 3/2008 |
| WO | WO 2010/141940 | 12/2010 |
| WO | WO 2013/188582 | 12/2013 |

OTHER PUBLICATIONS

Bell, "Structure and mechanism of *Escherichia coli* RecA ATPase", Sep. 19, 2005, *Molecular Microbiology*, 58(2):358-366.
Bianco et al., "DNA Strand Exchange Proteins: A Biochemical and Physical Comparison", Jun. 17, 1998, *Frontiers in Bioscience*, 3:d570-603.
Branden et al., "Introduction to Protein Structure," Garland Publishing Inc., New York; 1991; p. 247.
Farb et al., "Role of Allosteric Switch Residue Histidine 195 in Maintaining Active-Site Asyrnnetry in Presynaptic Filaments of Bacteriophage T4 UvsX Recombinase", *Journal of Molecular Biology*, vol. 385, No. 2, Jan. 16, 2009, 393-404.
Gajewski et al., "Crystal Structure of the Phage T4 Recombinase UvsX and Its Functional Interaction with the T4 SF2 Helicase UvsW", *Journal of Molecular Biology*, vol. 405, No. 1, Jan. 7, 2011, 65-76.
Guo et al., "Protein tolerance to random amino acid change," *PNAS*, Jun. 22, 2004; 101(25):9205-9210.
Liu et al., "Assembly and dynamics of the bacteriophage T4 homologous recombination machinery", 2010, *Virology Journal*, 7(357): 1-15.
Maher et al., "Coordinated Binding of Single-Stranded and Double-Stranded DNA by UvsX Recombinase", 2013, *PLOS One*, 8(6): e66654, 1-11.
Previte et al., "DNA sequencing using polymerase substrate-binding kinetics", *Nature Communications*, vol. 6, 5936, Jan. 23, 2015, 12 pages.
Sadowski et al., The sequence-structure relationship and protein function prediction, *Current Opinion in Structural Biology*, May 4, 2009; 19:357-362.
Seffernick et al., "Melamine Deaminase and Atrazine Chlorohydrolase: 98 Percent Identical but Functionally Different," *J. Bacteriol.*, Apr. 2001; 183(8):2405-2410.
Stefanska et al., "Discovery and characterization of RecA protein of thermophilic bacteriumThermus thermophilusMAT72 phage Tt72 that increases specificity of a PCR-based DNA amplification", *Journal of Biotechnology*, vol. 182, Apr. 28, 2014, 10 pages.
Witkowski et al., "Conversion of a β-Ketoacyl Synthase to a Malonyl Decarboxylase by Replacement of the Active-Site Cysteine with Glutamine," *Biochemistry*, Aug. 1999; 38:11643-11650.

*Primary Examiner* — Delia M Ramirez
(74) *Attorney, Agent, or Firm* — Mueting, Raasch & Gebhardt, P.A.

(57) ABSTRACT

Presented herein are recombinases for improved recombinase-mediated amplification of nucleic acids, such as a PCR-library having single-stranded adapter regions, on a patterned flow cell surface for improved cluster amplification, as well as methods and kits using the same.

18 Claims, 5 Drawing Sheets

Specification includes a Sequence Listing.

ALIGNMENT OF UvsX RELATIVES

```
           t4       MS--------------DLKSRLIKASTSKLTAELTASKFFNEKDV-VRTKIPMMNIALSGEI
           t6       MS-------------IADLKSRLIKASTSKMTAELTTSKFFNEKDV-IRTKIPMLNIAISGAI
        Phage133    MS--------------SLKERLIKASTSKMTAELTKSKFFNDKTV-VRTRIPMLNIAISGAL
           Rb69     MS--------------DLKSRLIKASTSKMTADLTKSKLFNNRDE-VPTRIPMLNIALGGAL
           Aeh1     MAKGIKTAKTGNLGSLMSKLAGTSSNKMSSVLADSKFFNDKDC-VRTRVPLLNLAMSGEL
           Ae65     MA----KKAKVVNSGDLLERLNGTSSNKMSAMLASSIFFNEKDT-IRTRVPIINLMMSGRL
           Kvp40    MS--------------DLMKSLKKSSTSGYAQVLSESQFMFDKDH-TRTYVPAIMIAPSGEV
           Rb43     MS--------------NKALLKKLIKNSMSQSAAILSESDVFNNITK-TRTRVPILNLALSGAF
           PSSM2    M---------------DFLKEIVKEIGDEYTQVAAD---IQENERFIDTGSYIFNGLVSGSI
           PSSM4    M---------------NFLKDIAKEIGNDYASLVSES/GAGDTAGFIDTGSYIFNALLSGSI
                    *                 .  .    :   .    .  .    *     *     .. * .

recA GPESSGKTTLT          Walker A
           t4       TGGMQSG-LLILAGPSKSFKSNFGLTMVSSYMRQYPDAVCLFYDSEFGITPAYLPSMGVD
           t6       DGGMQSG-LTIPAGPSKHFKSNMSLTMVAAYLNKYPDAVCLFYDSEFGITPAYLPSMGVD
        Phage133    MGGMQSG-LTIPAGPSKHFKSNMGLTMVAAYMKAFPDAVCMFYDSEFGITPAYLKAMGVD
           Rb69     NAGLQSG-LTIPAAPSKHFKTLPGLTMVAAYMKKYPDAICLFYDSEFGASESYFRSMGVD
           Aeh1     DGGLTPG-LTVLAGPSKHFKSNLSLVFVAAYLRKYPDAVCIFFDNEFGSTPGYFESQGVD
           Ae65     DGGITPG-LTCIAGPSKHFKSNLSLVMVSAYLRKYPKAVCLFFDNEFGSTPDYFTSQGVD
           Kvp40    DGGLTSG-LTVLAGPSKHFKSKLGLVGVAAYLKKYPDAVCVFIDTEPGITPSYLRSQGVD
           Rb43     DGGLTSG-LTLFAGPSKHFKSKLGLVTVGAYLKANEDAVCLFYDSEKGVTKSYLKSMGVD
           PSSM2    FGGVSSSRITAIAGESSTGKTYPSLAVVKNFLDNNPDGYCLYFDTEAAVNKGLLESRGID
           PSSM4    YGGIPNNKITAIAGETSTGKTFFCLGMVQHFLESNPDAGVIYFESESAISKQMIEDRGID
                     .*   .   .  *   . *:  :    *:     .**    .      . * :  *:*

DNA binding loop1         LIPKAEIEG
           t4       PERVIHTPVQSLEQLRIDMVNQLDAI----------ERGEKVVFIDSLGHLASKKETED
           t6       PERVIHTPIQSVEQLKIDMVNQLEAI----------SRGEKVIVFIDSIGNMASKKETED
        Phage133    PDRVIHTPVQSVEQLKIDMTNQLEEV----------KRGEKVIVFIDSIGNLASKKETED
           Rb69     LDRVIHTPIQSVEQLKVDMTNQLDAI----------ERGDKVIIFIDSIGNTASKKETED
           Aeh1     ISRVIHCPFKNISELKFDIVKKLEAI----------ERGDKVIVFVDSIGNAASKKEIDD
           Ae65     ISRVVHCPFIDVEELKFDIVKKLESI----------TRGDKVIIYIDSIGNVASEKELQD
           Kvp40    PDRVLHIQCESVERMKFBMANQLKDLAERKRAKKAGEEPDRVIPFIDSVGNVASAKEIDD
           Rb43     PDRVVYTRITTVEQLRNDVVSQLDAL----------ERGDKVIIFVDSVGNTASKKELAD
           PSSM2    MNRLVVVNVVTIEEFRSKALRAVDIY-----LKTSEEERKPCMFVLDSLGNLSTEKEIRD
           PSSM4    SNRMLLVPVTTVQEFRLQAIKILDKY-----NEQTASERKPLMFVLDSLGNLSTSKEVED
                     .*:;    .     (::;.       :.  :** ;*   ::  **  *

DNA binding loop2
                     EIGDSHMG                      recA LNQIRMKIGVMFGNPETTTGG
           t4       ALNEKVVSDMTRAKIMKSLFRIVTPYFSTKNIPCIAINHT-YETQEMF-SKTVMQGGTGP
           t6       ALNEKSVADMTRAKSLKSLFRIVTPYFSIKNIPCVAYNIT-IETIEMF-SKTVMTGSTGV
        Phage133    ALNEKTTADMTRAKALKSLFRIVTPYFSIKDIPCVAYNNT-LQTLEMF-SKEVMTGSTGV
           Rb69     ALNEKVVSDMSRAKALKSLFRIVTPYLTIKDIPCVAIHNTAMEIGGLY-PKEIMGGGTGI
           Aeh1     AIDEKSVSDMTRAKQIKSLTRMMTPYLTVNDIPAIMVAHT-YDTQEMY-SKKVVSGGTGI
           Ae65     AKDEKSAQDMTRAKQIKSLFRMVTPYLTVLDIPCIAVYNT-YETQEMF-SKTVMSGGTGP
           Kvp40    AGNEKSVADMSRAKQLKSLFRIITPFYFTMLDIPCIAIRHT-YQTQEIY-SKTVMSGGTGI
           Rb43     ALSDNDKQDMTRAKALKGMFRMVTPYLADLDIPMVCIQHT-YDTQEMY-SKKVISGGTGL
           PSSM2    ALDDKQVRDMTKSQLVKGAFRMLTLKLGQANIPLIVTNHT-YDVIGSYVPTKEMGGGSGL
           PSSM4    SEAGKETRDMTRAQVVKSIPRVLTLKLGKANVPLIVTNHT-YDVVGAYIPTKEMGGGSGL
                     :       ::      *:   *;;*   :    ::*    :**    :   :  :  *
```

Fig. 1A

ALIGNMENT OF UvsX RELATIVES

```
t4        MYSADTVFIIGKRQIKDGSDLQGYQFVLNVEKSRTVKEKSKFFIDVKFD-GGIDPYSGLL
t6        MYSADTVFIIGKRQIKDGSDLQGYQFVLNVEKSRTVKEKSKFFIDVKFD-GGIDPYSGLL
Phage133  MYSADTVFFIGKRQVKDGTELAGYEFILKAEKSRMVKEKSVEFITVKFD-GGIDPYSGLL
Rb69      LYSANTVFPISKRQVKEGTELTGYDPTLKAEKSRTVKEKSTEFITVNFD-GGIDPFSGLL
Aeh1      TYSSDTVIIIGRQQEKDGKELLGYNFVLNMEKSRFVREQSKILLEVTFQ-GGINTYSGML
Ae65      NYSADTVIILGKQQDKDGKELLGYNFVMNAEKSRAIKEKSKILMVSFE-GGINTYSGLL
Kvp40     MYSADTVIILGKQQEKDGKDIIGYHFIMNIEKSRFVKEKMKVLTVTYE-NGIDPFSGLL
Rb43      MYSADTAIILGKQQVKEGTEVVGYDFIMNIEKSRFVKEKSKFLNVTYE-GGISMYSGLL
PSSM2     KYAASTIIYLSKKKEKDQKEVIGNLIKAKTHKSRLSKENKEVQIRLYYDERGLDRYYGLL
PSSM4     KYAASTIVYLSKKKEKNGKEVVGNIIKCKTAKSRLTKENSDVETRLYYD-RGLDRYYGLL
          *::.*  ::::: *: ::: *   :  :   *  :   ::) *;: : *;* t4        DMALELGFVVKPKNGWYAREPLDEETGEMI--REEKSWRAKDTNCTTFWGPLFKHQPFRD
t6        DMALELGFVVKPKNGWYAREPLDEETGEMI--REEKSWRAKDTNCTTFWGPLFKHQPFRD
Phage133  EMATDLGFVVKPKVGWYKRAMMVD--GVMQ--HEEKSWRAKDTDSIDFWGPLFKHDEPRK
Rb69      EMATEIGPVVKPKAGWYAREPLDEETGEMI--REEKSWRAKATDCVEFWGPLFKHKPFRD
Aeh1      DIALRVGFVVKPSNGWFSRAPLDEETGELV--EEDFKWRRADTNCLEFWKPMFAHQPFKT
Ae65      KIAQELGFVTKPQNARYQRNPLDLEPGENVIPEDEFKWTEEESDSLEFWKPMFSHKPFMD
Kvp40     DIALQTGHVVKPSNGWYQRATVDEETGEMI--VEEKKYEAKETQTISFWKDIINSPTFKE
Rb43      DLAMEMNPVQTPTKGWRGRAFLNTETGELE--LEEEKWRESETNSIEFWRPLFTHQPFLD
PSSM2     ELG-EIGGMWKNVAGRYRMNGKKIYAKEIL--KNPTEYPTDDI-----------MEQLDN
PSSM4     ELG-EKHGVPSRKGNRVVVGDSSVYPSAIL--ADPEKYFTEEL-----------NEKLDS
          .:.  :  :.                       :   : .:                :

t4        AIKRAYQLGAIDSNEIVEAEVDELINSKVEKFKSP--ESKSKSAADLETDLEQLSDMEEP
t6        AIKRAYQLGAIDSNEIVEAEVDELINSKVEKFKSP--ESKSKSAADLETDLEQLSDMEEP
Phage133  AIETRYQLGSIESDAEVDAEVDALIGSKTTAKISGVNFGPAESAADKEQQLEDFVD----
Rb69      AIETKYKLQAISSIKEVDDAVNDLINCKATTKV-PVKTSDAPSAADIENDLDEMED---P
Aeh1      ACSDMFKLKSVAVKDEVFDRVDELFSGEAEMPVNMGRKLDTADQEEIDQLEEVDEGSDS
Ae65      AVSNAYKLKAVEVSQRVFDEVDQLPG----------------------------------
Kvp40     GVRRIYCLGQLD-ESELFGEVDSLPD----------------------------------
Rb43      AIQDKYRIPDKEITDG--AALEDLYSTDEPESNKIDLDDDIPDDIGIDQDEEPIM-----
PSSM2     IAKEHFSYGTN-------------------------------------------------
PSSM4     AAAKEFRYGN--------------------------------------------------
                :

t4        NE------
t6        NE------
Phage133  ED------
Rb69      DE------
Aeh1      DELPANLD
Ae65      --------
Kvp40     --------
Rb43      --------
PSSM2     --------
PSSM4     --------
```

Fig. 1B

```
RB49    MS-VLEKLKKNSTLKTTAVLSKSSFFNEKTNTRTKIPMLNIAFSGDLKKGFQSGLIFFAGPSKHFK   65
T4      MSDLKSRLIKASTSKLTAELTASKFFNEKDVVRTKIPMMNIALSGEITGGMQSGLLILAGPSKSFK   66

RB49    SNMGLTCVSAYMKQNPDAACLFFDSEFGITSAYLESMGVDPDRVVHVPIKNIEELKFEIM        125
T4      SNFGLTMVSSYMRQYPDAVCLFYDSEFGITPAYLRSMGVDPERVIHTPVQSLEQLRIDMV        126

RB49    NQLEQITREDKVIIFIDSIGNLASKKEVEDAINEKSAQDMTRAKALKGLFRMVTPYLTMN        185
T4      NQLDAIERGEKVVVFIDSLGNLASKKETEDALNEKVVSDMTRAKTMKSLFRIVTPYFSTK        186

RB49    DIPCIAINHTYETQEMFSKTVMSGGTGAMYSANEVFIIGRRQQKEGTEITGYDFILNAEK        245
T4      NIPCIAINHTYETQEMFSKTVMGGGTGPMYSADTVFIIGKRQIKDGSDLQGYQFVLNVEK        246

RB49    SRTVKEKSKFISVTFSGGIDPYSGLLELAVELGWVVKPSNGWYSRSILNTETGEMETEE        305
T4      SRTVKEKSKFIDVKFDGGIDPYSGLLDMALELGFVVKPKNGWYAREFLDEETGEMIREE         306

RB49    RKFRAKETNSIEFWKPLLTNDKFNEAINDHYKLGQVISDEAVDKEIEDML                  355
T4      KSWRAKDTNCTTFWGPLFKHQPFRDAIKRAYQLGAIDSNEIVEAEVDELI                  356
```

Fig. 2

SEQUENCE LISTING

<160> NUMBER OF SEQ ID NOS: 35

<210> SEQ ID NO 1
<211> LENGTH: 356
<212> TYPE: PRT
<213> ORGANISM: Enterobacteria phage RB49

<400> SEQUENCE: 1

```
Met Ser Val Leu Glu Lys Leu Lys Lys Asn Ser Thr Leu Lys Thr Thr
1               5                   10                  15

Ala Val Leu Ser Lys Ser Ser Phe Phe Asn Glu Lys Thr Asn Thr Arg
            20                  25                  30

Thr Lys Ile Pro Met Leu Asn Ile Ala Phe Ser Gly Asp Leu Lys Lys
        35                  40                  45

Gly Phe Gln Ser Gly Leu Ile Phe Phe Ala Gly Pro Ser Lys His Phe
    50                  55                  60

Lys Ser Asn Met Gly Leu Thr Cys Val Ser Ala Tyr Met Lys Gln Asn
65                  70                  75                  80

Pro Asp Ala Ala Cys Leu Phe Phe Asp Ser Glu Phe Gly Ile Thr Ser
                85                  90                  95

Ala Tyr Leu Glu Ser Met Gly Val Asp Pro Asp Arg Val Val His Val
            100                 105                 110

Pro Ile Lys Asn Ile Glu Glu Leu Lys Phe Glu Ile Met Asn Gln Leu
        115                 120                 125

Glu Gln Ile Thr Arg Glu Asp Lys Val Ile Ile Phe Ile Asp Ser Ile
    130                 135                 140

Gly Asn Leu Ala Ser Lys Lys Glu Val Glu Asp Ala Ile Asn Glu Lys
145                 150                 155                 160

Ser Ala Gln Asp Met Thr Arg Ala Lys Ala Leu Lys Gly Leu Phe Arg
                165                 170                 175

Met Val Thr Pro Tyr Leu Thr Met Asn Asp Ile Pro Cys Ile Ala Ile
            180                 185                 190

Asn His Thr Tyr Glu Thr Gln Glu Met Phe Ser Lys Thr Val Met Ser
        195                 200                 205

Gly Gly Thr Gly Ala Met Tyr Ser Ala Asn Glu Val Phe Ile Ile Gly
    210                 215                 220

Arg Arg Gln Gln Lys Glu Gly Thr Glu Ile Thr Gly Tyr Asp Phe Ile
225                 230                 235                 240

Leu Asn Ala Glu Lys Ser Arg Thr Val Lys Glu Lys Ser Lys Phe Pro
                245                 250                 255
```

```
Ile Ser Val Thr Phe Ser Gly Gly Ile Asp Pro Tyr Ser Gly Leu Leu
            260                 265                 270

Glu Leu Ala Val Glu Leu Gly Trp Val Val Lys Pro Ser Asn Gly Trp
        275                 280                 285

Tyr Ser Arg Ser Ile Leu Asn Thr Gly Thr Gly Glu Met Glu Thr Glu
        290                 295                 300

Glu Arg Lys Phe Arg Ala Lys Glu Thr Asn Ser Ile Glu Phe Trp Lys
305                 310                 315                 320

Pro Leu Leu Thr Asn Asp Lys Phe Asn Glu Ala Ile Asn Asp His Tyr
                325                 330                 335

Lys Leu Gly Gln Val Ile Ser Asp Glu Ala Val Asp Lys Glu Ile Glu
            340                 345                 350

Asp Met Leu Ala
            355

<210> SEQ ID NO 2
<211> LENGTH: 356
<212> TYPE: PRT
<213> ORGANISM: Enterobacteria phage RB49

<400> SEQUENCE: 2

Met Ser Val Leu Glu Lys Leu Lys Lys Asn Ser Thr Leu Lys Thr Thr
1               5                   10                  15

Ala Val Leu Ser Lys Ser Ser Phe Phe Asn Glu Lys Thr Asn Thr Arg
            20                  25                  30

Thr Lys Ile Pro Met Leu Asn Ile Ala Phe Ser Gly Asp Leu Lys Lys
        35                  40                  45

Gly Phe Gln Ser Gly Leu Ile Phe Phe Ala Gly Pro Ser Lys Ser Phe
    50                  55                  60

Lys Ser Asn Met Gly Leu Thr Cys Val Ser Ala Tyr Met Lys Gln Asn
65                  70                  75                  80

Pro Asp Ala Ala Cys Leu Phe Phe Asp Ser Glu Phe Gly Ile Thr Ser
                85                  90                  95

Ala Tyr Leu Glu Ser Met Gly Val Asp Pro Asp Arg Val Val His Val
            100                 105                 110

Pro Ile Lys Asn Ile Glu Glu Leu Lys Phe Glu Ile Met Asn Gln Leu
        115                 120                 125

Glu Gln Ile Thr Arg Glu Asp Lys Val Ile Ile Phe Ile Asp Ser Ile
    130                 135                 140

Gly Asn Leu Ala Ser Lys Lys Glu Val Glu Asp Ala Ile Asn Glu Lys
145                 150                 155                 160

Ser Ala Gln Asp Met Thr Arg Ala Lys Ala Leu Lys Gly Leu Phe Arg
                165                 170                 175

Met Val Thr Pro Tyr Leu Thr Met Asn Asp Ile Pro Cys Ile Ala Ile
            180                 185                 190

Asn His Thr Tyr Glu Thr Gln Glu Met Phe Ser Lys Thr Val Met Ser
        195                 200                 205

Gly Gly Thr Gly Ala Met Tyr Ser Ala Asn Glu Val Phe Ile Ile Gly
    210                 215                 220

Arg Arg Gln Gln Lys Glu Gly Thr Glu Ile Thr Gly Tyr Asp Phe Ile
225                 230                 235                 240

Leu Asn Ala Glu Lys Ser Arg Thr Val Lys Glu Lys Ser Lys Phe Lys
                245                 250                 255

Ile Ser Val Thr Phe Ser Gly Gly Ile Asp Pro Tyr Ser Gly Leu Leu
```

```
                      260                 265                 270
Glu Leu Ala Val Glu Leu Gly Trp Val Val Lys Pro Ser Asn Gly Trp
            275                 280                 285

Tyr Ser Arg Ser Ile Leu Asn Thr Glu Thr Gly Glu Met Glu Thr Glu
            290                 295                 300

Glu Arg Lys Phe Arg Ala Lys Glu Thr Asn Ser Ile Glu Phe Trp Lys
305                 310                 315                 320

Pro Leu Leu Thr Asn Asp Lys Phe Asn Glu Ala Ile Asn Asp His Tyr
                325                 330                 335

Lys Leu Gly Gln Val Ile Ser Asp Glu Ala Val Asp Lys Glu Ile Glu
            340                 345                 350

Asp Met Leu Ala
        355

<210> SEQ ID NO 3
<211> LENGTH: 8
<212> TYPE: PRT
<213> ORGANISM: Artificial Sequence
<220> FEATURE:
<223> OTHER INFORMATION: Semi Conserved Domain

<400> SEQUENCE: 3

Lys Glu Lys Ser Lys Phe Phe Ile
1               5

<210> SEQ ID NO 4
<211> LENGTH: 8
<212> TYPE: PRT
<213> ORGANISM: Artificial Sequence
<220> FEATURE:
<223> OTHER INFORMATION: Semi Conserved Domain

<400> SEQUENCE: 4

Lys Glu Lys Ser Lys Phe Pro Ile
1               5

<210> SEQ ID NO 5
<211> LENGTH: 8
<212> TYPE: PRT
<213> ORGANISM: Artificial Sequence
<220> FEATURE:
<223> OTHER INFORMATION: Semi Conserved Domain
<220> FEATURE:
<221> NAME/KEY: VARIANT
<222> LOCATION: (5)..(5)
<223> OTHER INFORMATION: X = any AA
<220> FEATURE:
<221> NAME/KEY: VARIANT
<222> LOCATION: (7)..(7)
<223> OTHER INFORMATION: X = any AA

<400> SEQUENCE: 5

Lys Glu Lys Ser Xaa Phe Xaa Ile
1               5

<210> SEQ ID NO 6
<211> LENGTH: 13
<212> TYPE: PRT
<213> ORGANISM: Artificial Sequence
<220> FEATURE:
<223> OTHER INFORMATION: Semi Conserved Domain
<220> FEATURE:
<221> NAME/KEY: VARIANT
<222> LOCATION: (4)..(4)
<223> OTHER INFORMATION: X = any AA
<220> FEATURE:
```

```
<221> NAME/KEY: VARIANT
<222> LOCATION: (5)..(5)
<223> OTHER INFORMATION: X = any AA
<220> FEATURE:
<221> NAME/KEY: VARIANT
<222> LOCATION: (8)..(8)
<223> OTHER INFORMATION: X = any AA
<220> FEATURE:
<221> NAME/KEY: VARIANT
<222> LOCATION: (9)..(9)
<223> OTHER INFORMATION: X = any AA
<220> FEATURE:
<221> NAME/KEY: VARIANT
<222> LOCATION: (10)..(10)
<223> OTHER INFORMATION: X = any AA
<220> FEATURE:
<221> NAME/KEY: VARIANT
<222> LOCATION: (11)..(11)
<223> OTHER INFORMATION: X = any AA
<220> FEATURE:
<221> NAME/KEY: VARIANT
<222> LOCATION: (12)..(12)
<223> OTHER INFORMATION: X = any AA
<220> FEATURE:
<221> NAME/KEY: VARIANT
<222> LOCATION: (13)..(13)
<223> OTHER INFORMATION: X = any AA

<400> SEQUENCE: 6

Lys Ser Arg Xaa Xaa Lys Glu Xaa Xaa Xaa Xaa Xaa Xaa
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Semi Conserved Domain

<400> SEQUENCE: 7

Lys Ser Arg Thr Val Lys Glu Lys Ser Lys Phe Phe Ile
1               5                   10

<210> SEQ ID NO 8
<211> LENGTH: 391
<212> TYPE: PRT
<213> ORGANISM: Enterobacteria phage T4

<400> SEQUENCE: 8

Met Ser Asp Leu Lys Ser Arg Leu Ile Lys Ala Ser Thr Ser Lys Leu
1               5                   10                  15

Thr Ala Glu Leu Thr Ala Ser Lys Phe Phe Asn Glu Lys Asp Val Val
            20                  25                  30

Arg Thr Lys Ile Pro Met Met Asn Ile Ala Leu Ser Gly Glu Ile Thr
        35                  40                  45

Gly Gly Met Gln Ser Gly Leu Leu Ile Leu Ala Gly Pro Ser Lys Ser
    50                  55                  60

Phe Lys Ser Asn Phe Gly Leu Thr Met Val Ser Ser Tyr Met Arg Gln
65                  70                  75                  80

Tyr Pro Asp Ala Val Cys Leu Phe Tyr Asp Ser Glu Phe Gly Ile Thr
                85                  90                  95

Pro Ala Tyr Leu Arg Ser Met Gly Val Asp Pro Glu Arg Val Ile His
            100                 105                 110

Thr Pro Val Gln Ser Leu Glu Gln Leu Arg Ile Asp Met Val Asn Gln
        115                 120                 125

Leu Asp Ala Ile Glu Arg Gly Glu Lys Val Val Val Phe Ile Asp Ser
```

```
        130                 135                 140
Leu Gly Asn Leu Ala Ser Lys Lys Glu Thr Glu Asp Ala Leu Asn Glu
145                 150                 155                 160

Lys Val Val Ser Asp Met Thr Arg Ala Lys Thr Met Lys Ser Leu Phe
                165                 170                 175

Arg Ile Val Thr Pro Tyr Phe Ser Thr Lys Asn Ile Pro Cys Ile Ala
                180                 185                 190

Ile Asn His Thr Tyr Glu Thr Gln Glu Met Phe Ser Lys Thr Val Met
            195                 200                 205

Gly Gly Gly Thr Gly Pro Met Tyr Ser Ala Asp Thr Val Phe Ile Ile
        210                 215                 220

Gly Lys Arg Gln Ile Lys Asp Gly Ser Asp Leu Gln Gly Tyr Gln Phe
225                 230                 235                 240

Val Leu Asn Val Glu Lys Ser Arg Thr Val Lys Glu Lys Ser Lys Phe
                245                 250                 255

Phe Ile Asp Val Lys Phe Asp Gly Gly Ile Asp Pro Tyr Ser Gly Leu
                260                 265                 270

Leu Asp Met Ala Leu Glu Leu Gly Phe Val Val Lys Pro Lys Asn Gly
            275                 280                 285

Trp Tyr Ala Arg Glu Phe Leu Asp Glu Glu Thr Gly Glu Met Ile Arg
        290                 295                 300

Glu Glu Lys Ser Trp Arg Ala Lys Asp Thr Asn Cys Thr Thr Phe Trp
305                 310                 315                 320

Gly Pro Leu Phe Lys His Gln Pro Phe Arg Asp Ala Ile Lys Arg Ala
                325                 330                 335

Tyr Gln Leu Gly Ala Ile Asp Ser Asn Glu Ile Val Glu Ala Glu Val
            340                 345                 350

Asp Glu Leu Ile Asn Ser Lys Val Glu Lys Phe Lys Ser Pro Glu Ser
        355                 360                 365

Lys Ser Lys Ser Ala Ala Asp Leu Glu Thr Asp Leu Glu Gln Leu Ser
370                 375                 380

Asp Met Glu Glu Phe Asn Glu
385                 390

<210> SEQ ID NO 9
<211> LENGTH: 393
<212> TYPE: PRT
<213> ORGANISM: Enterobacteria phage T6

<400> SEQUENCE: 9

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
                20                  25                  30

Val Ile Arg Thr Lys Ile Pro Met Leu Asn Ile Ala Ile Ser Gly Ala
            35                  40                  45

Ile Asp Gly Gly Met Gln Ser Gly Leu Thr Ile Phe Ala Gly Pro Ser
        50                  55                  60

Lys His Phe Lys Ser Asn Met Ser Leu Thr Met Val Ala Ala Tyr Leu
65                  70                  75                  80

Asn Lys Tyr Pro Asp Ala Val Cys Leu Phe Tyr Asp Ser Glu Phe Gly
                85                  90                  95

Ile Thr Pro Ala Tyr Leu Arg Ser Met Gly Val Asp Pro Glu Arg Val
                100                 105                 110
```

```
Ile His Thr Pro Ile Gln Ser Val Glu Gln Leu Lys Ile Asp Met Val
            115                 120                 125

Asn Gln Leu Glu Ala Ile Glu Arg Gly Glu Lys Val Ile Val Phe Ile
        130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Gly Ile Asp Pro Tyr Ser
            260                 265                 270

Gly Leu Leu Asp Met Ala Leu Glu Leu Gly Phe Val Val Lys Pro Lys
        275                 280                 285

Asn Gly Trp Tyr Ala Arg Glu Phe Leu Asp Glu Glu Thr Gly Glu Met
        290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Lys Phe Lys Ser Pro
        355                 360                 365

Glu Ser Lys Ser Lys Ser Ala Ala Asp Leu Glu Thr Asp Leu Glu Gln
        370                 375                 380

Leu Ser Asp Met Glu Glu Phe Asn Glu
385                 390

<210> SEQ ID NO 10
<211> LENGTH: 387
<212> TYPE: PRT
<213> ORGANISM: Acinetobacter phage 133

<400> SEQUENCE: 10

Met Ser Ser Leu Lys Glu Arg Leu Ile Lys Ala Ser Thr Ser Lys Met
1               5                   10                  15

Thr Ala Glu Leu Thr Lys Ser Lys Phe Phe Asn Asp Lys Thr Val Val
            20                  25                  30

Arg Thr Arg Ile Pro Met Leu Asn Ile Ala Ile Ser Gly Ala Leu Asn
        35                  40                  45

Gly Gly Met Gln Ser Gly Leu Thr Ile Phe Ala Gly Pro Ser Lys His
    50                  55                  60

Phe Lys Ser Asn Met Gly Leu Thr Met Val Ala Ala Tyr Met Lys Ala
65                  70                  75                  80

Phe Pro Asp Ala Val Cys Met Phe Tyr Asp Ser Glu Phe Gly Ile Thr
                85                  90                  95
```

```
Pro Ala Tyr Leu Lys Ala Met Gly Val Asp Pro Arg Val Ile His
            100                 105                 110
Thr Pro Val Gln Ser Val Glu Gln Leu Lys Ile Asp Met Thr Asn Gln
            115                 120                 125
Leu Glu Glu Val Lys Arg Gly Glu Lys Val Ile Val Phe Ile Asp Ser
    130                 135                 140
Ile Gly Asn Leu Ala Ser Lys Lys Glu Thr Glu Asp Ala Leu Asn Glu
145                 150                 155                 160
Lys Thr Thr Ala Asp Met Thr Arg Ala Lys Ala Leu Lys Ser Leu Phe
                165                 170                 175
Arg Ile Val Thr Pro Tyr Phe Ser Ile Lys Asp Ile Pro Cys Val Ala
                180                 185                 190
Val Asn His Thr Leu Gln Thr Leu Glu Met Phe Ser Lys Glu Val Met
            195                 200                 205
Thr Gly Gly Thr Gly Val Met Tyr Ser Ala Asp Thr Val Phe Phe Ile
    210                 215                 220
Gly Lys Arg Gln Val Lys Asp Gly Thr Glu Leu Ala Gly Tyr Glu Phe
225                 230                 235                 240
Ile Leu Lys Ala Glu Lys Ser Arg Met Val Lys Glu Lys Ser Val Phe
                245                 250                 255
Pro Ile Thr Val Lys Phe Asp Gly Gly Ile Asp Pro Tyr Ser Gly Leu
                260                 265                 270
Leu Glu Met Ala Thr Asp Leu Gly Phe Val Val Lys Pro Lys Val Gly
            275                 280                 285
Trp Tyr Lys Arg Ala Met Met Val Asp Gly Val Met Gln His Glu Glu
        290                 295                 300
Lys Ser Trp Arg Ala Lys Asp Thr Asp Ser Ile Asp Phe Trp Gly Pro
305                 310                 315                 320
Leu Phe Lys His Asp Glu Phe Arg Lys Ala Ile Glu Thr Arg Tyr Gln
                325                 330                 335
Leu Gly Ser Ile Glu Ser Asp Ala Glu Val Asp Ala Glu Val Asp Ala
                340                 345                 350
Leu Ile Gly Ser Lys Thr Thr Ala Lys Ile Ser Gly Val Asn Phe Gly
            355                 360                 365
Pro Ala Glu Ser Ala Ala Asp Lys Glu Gln Gln Leu Glu Asp Phe Val
    370                 375                 380
Asp Glu Asp
385

<210> SEQ ID NO 11
<211> LENGTH: 390
<212> TYPE: PRT
<213> ORGANISM: Enterobacteria phage RB69

<400> SEQUENCE: 11

Met Ser Asp Leu Lys Ser Arg Leu Ile Lys Ala Ser Thr Ser Lys Met
1               5                   10                  15
Thr Ala Asp Leu Thr Lys Ser Lys Leu Phe Asn Asn Arg Asp Glu Val
            20                  25                  30
Pro Thr Arg Ile Pro Met Leu Asn Ile Ala Leu Gly Ala Leu Asn
            35                  40                  45
Ala Gly Leu Gln Ser Gly Leu Thr Ile Phe Ala Ala Pro Ser Lys His
    50                  55                  60
Phe Lys Thr Leu Phe Gly Leu Thr Met Val Ala Ala Tyr Met Lys Lys
```

65                  70                  75                  80
        Tyr Lys Asp Ala Ile Cys Leu Phe Tyr Asp Ser Glu Phe Gly Ala Ser
                        85                  90                  95

Glu Ser Tyr Phe Arg Ser Met Gly Val Asp Leu Asp Arg Val Val His
                    100                 105                 110

Thr Pro Ile Gln Ser Val Glu Gln Leu Lys Val Asp Met Thr Asn Gln
                115                 120                 125

Leu Asp Ala Ile Glu Arg Gly Asp Lys Val Ile Phe Ile Asp Ser
            130                 135                 140

Ile Gly Asn Thr Ala Ser Lys Lys Glu Thr Glu Asp Ala Leu Asn Glu
        145                 150                 155                 160

Lys Val Val Gly Asp Met Ser Arg Ala Lys Ala Leu Lys Ser Leu Phe
                        165                 170                 175

Arg Ile Val Thr Pro Tyr Leu Thr Ile Lys Asp Ile Pro Cys Val Ala
                    180                 185                 190

Ile Asn His Thr Ala Met Glu Ile Gly Gly Leu Tyr Pro Lys Glu Ile
                195                 200                 205

Met Gly Gly Gly Thr Gly Ile Leu Tyr Ser Ala Asn Thr Val Phe Phe
            210                 215                 220

Ile Ser Lys Arg Gln Val Lys Glu Gly Thr Glu Leu Thr Gly Tyr Asp
        225                 230                 235                 240

Phe Thr Leu Lys Ala Glu Lys Ser Arg Thr Val Lys Glu Lys Ser Thr
                        245                 250                 255

Phe Pro Ile Thr Val Asn Phe Asp Gly Gly Ile Asp Pro Phe Ser Gly
                    260                 265                 270

Leu Leu Glu Met Ala Thr Glu Ile Gly Phe Val Val Lys Pro Lys Ala
                275                 280                 285

Gly Trp Tyr Ala Arg Glu Phe Leu Asp Glu Thr Gly Glu Met Ile
            290                 295                 300

Arg Glu Glu Lys Ser Trp Arg Ala Lys Ala Thr Asp Cys Val Glu Phe
        305                 310                 315                 320

Trp Gly Pro Leu Phe Lys His Lys Pro Phe Arg Asp Ala Ile Glu Thr
                        325                 330                 335

Lys Tyr Lys Leu Gly Ala Ile Ser Ser Ile Lys Glu Val Asp Asp Ala
                    340                 345                 350

Val Asn Asp Leu Ile Asn Cys Lys Ala Thr Thr Lys Val Pro Val Lys
                355                 360                 365

Thr Ser Asp Ala Pro Ser Ala Ala Asp Ile Glu Asn Asp Leu Asp Glu
            370                 375                 380

Met Glu Asp Phe Asp Glu
        385                 390

<210> SEQ ID NO 12
<211> LENGTH: 411
<212> TYPE: PRT
<213> ORGANISM: Aeromonas phage Aeh1

<400> SEQUENCE: 12

Met Ala Lys Gly Ile Lys Thr Ala Lys Thr Gly Asn Leu Gly Ser Leu
        1               5                   10                  15

Met Ser Lys Leu Ala Gly Thr Ser Ser Asn Lys Met Ser Ser Val Leu
                    20                  25                  30

Ala Asp Ser Lys Phe Phe Asn Asp Lys Asp Cys Val Arg Thr Arg Val
                35                  40                  45

-continued

```
Pro Leu Leu Asn Leu Ala Met Ser Gly Glu Leu Asp Gly Gly Leu Thr
 50                  55                  60

Pro Gly Leu Thr Val Leu Ala Gly Pro Ser Lys His Phe Lys Ser Asn
 65                  70                  75                  80

Leu Ser Leu Val Phe Ala Ala Tyr Leu Arg Lys Tyr Pro Asp Ala
                 85                  90                  95

Val Cys Ile Phe Phe Asp Asn Glu Phe Gly Ser Thr Pro Gly Tyr Phe
                100                 105                 110

Glu Ser Gln Gly Val Asp Ile Ser Arg Val Ile His Cys Pro Phe Lys
                115                 120                 125

Asn Ile Glu Glu Leu Lys Phe Asp Ile Val Lys Leu Glu Ala Ile
130                 135                 140

Glu Arg Gly Asp Arg Val Ile Val Phe Val Asp Ser Ile Gly Asn Ala
145                 150                 155                 160

Ala Ser Lys Lys Glu Ile Asp Asp Ala Ile Asp Glu Lys Ser Val Ser
                165                 170                 175

Asp Met Thr Arg Ala Lys Gln Ile Lys Ser Leu Thr Arg Met Met Thr
                180                 185                 190

Pro Tyr Leu Thr Val Asn Asp Ile Pro Ala Ile Met Val Ala His Thr
                195                 200                 205

Tyr Asp Thr Gln Glu Met Tyr Ser Lys Lys Val Val Ser Gly Gly Thr
210                 215                 220

Gly Ile Thr Tyr Ser Ser Asp Thr Val Ile Ile Gly Arg Gln Gln
225                 230                 235                 240

Glu Lys Asp Gly Lys Glu Leu Leu Gly Tyr Asn Phe Val Leu Asn Met
                245                 250                 255

Glu Lys Ser Arg Phe Val Lys Glu Gln Ser Lys Leu Pro Leu Glu Val
                260                 265                 270

Thr Phe Gln Gly Gly Ile Asn Thr Tyr Ser Gly Met Leu Asp Ile Ala
                275                 280                 285

Leu Glu Val Gly Phe Val Val Lys Pro Ser Asn Gly Trp Phe Ser Arg
                290                 295                 300

Ala Phe Leu Asp Glu Glu Thr Gly Glu Leu Val Glu Glu Asp Arg Lys
305                 310                 315                 320

Trp Arg Arg Ala Asp Thr Asn Cys Leu Glu Phe Trp Lys Pro Met Phe
                325                 330                 335

Ala His Gln Pro Phe Lys Thr Ala Cys Ser Asp Met Phe Lys Leu Lys
                340                 345                 350

Ser Val Ala Val Lys Asp Glu Val Phe Asp Glu Val Asp Glu Leu Phe
                355                 360                 365

Ser Gly Glu Ala Glu Met Pro Val Asn Met Gly Arg Lys Leu Asp Thr
                370                 375                 380

Ala Asp Gln Glu Glu Ile Asp Gln Leu Glu Glu Val Asp Val Glu Gly
385                 390                 395                 400

Ser Asp Ser Asp Glu Leu Phe Ala Asn Leu Asp
                405                 410

<210> SEQ ID NO 13
<211> LENGTH: 368
<212> TYPE: PRT
<213> ORGANISM: Aeromonas phage 65

<400> SEQUENCE: 13

Met Ala Lys Lys Ala Lys Val Val Asn Ser Gly Asp Leu Leu Glu Arg
 1               5                  10                  15
```

Leu Asn Gly Thr Ser Ser Asn Lys Met Ser Ala Met Leu Ala Glu Ser
    20                  25                  30

Ile Phe Phe Asn Glu Lys Asp Thr Ile Arg Thr Arg Val Pro Ile Ile
        35                  40                  45

Asn Leu Met Met Ser Gly Arg Leu Asp Gly Ile Thr Pro Gly Leu
50                  55                  60

Thr Cys Ile Ala Gly Pro Ser Lys His Phe Lys Ser Asn Leu Ser Leu
65                  70                  75                  80

Val Met Val Ser Ala Tyr Leu Arg Lys Tyr Pro Lys Ala Val Cys Leu
                85                  90                  95

Phe Phe Asp Asn Glu Phe Gly Ser Thr Pro Asp Tyr Phe Thr Ser Gln
            100                 105                 110

Gly Val Asp Ile Ser Arg Val Val His Cys Pro Phe Ile Asp Val Glu
        115                 120                 125

Glu Leu Lys Phe Asp Ile Val Lys Lys Leu Glu Ser Ile Thr Arg Gly
130                 135                 140

Asp Lys Val Ile Ile Tyr Ile Asp Ser Ile Gly Asn Val Ala Ser Lys
145                 150                 155                 160

Lys Glu Leu Gln Asp Ala Lys Asp Glu Lys Ser Ala Gln Asp Met Thr
                165                 170                 175

Arg Ala Lys Gln Ile Lys Ser Leu Phe Arg Met Val Thr Pro Tyr Leu
            180                 185                 190

Thr Val Leu Asp Ile Pro Cys Ile Ala Val Asn His Thr Tyr Glu Thr
        195                 200                 205

Gln Glu Met Phe Ser Lys Thr Val Met Ser Gly Gly Thr Gly Pro Met
210                 215                 220

Tyr Ser Ala Asp Thr Val Ile Ile Leu Gly Lys Gln Gln Asp Lys Asp
225                 230                 235                 240

Gly Lys Glu Leu Leu Gly Tyr Asn Phe Val Met Asn Ala Glu Lys Ser
                245                 250                 255

Arg Ala Ile Lys Glu Lys Ser Lys Leu Asp Leu Met Val Ser Phe Glu
            260                 265                 270

Gly Gly Ile Asn Thr Tyr Ser Gly Leu Leu Lys Ile Ala Gln Glu Leu
        275                 280                 285

Gly Phe Val Thr Lys Pro Gln Asn Ala Arg Tyr Gln Arg Asn Phe Leu
290                 295                 300

Asp Leu Glu Pro Gly Glu Met Val Ile Pro Glu Asp Glu Lys Lys Trp
305                 310                 315                 320

Thr Glu Glu Glu Ser Asp Ser Leu Glu Phe Trp Lys Pro Met Phe Ser
                325                 330                 335

His Lys Pro Phe Met Asp Ala Val Ser Asn Ala Tyr Lys Leu Lys Ala
            340                 345                 350

Val Glu Val Ser Gln Glu Val Phe Asp Glu Val Asp Gln Leu Phe Gly
        355                 360                 365

<210> SEQ ID NO 14
<211> LENGTH: 366
<212> TYPE: PRT
<213> ORGANISM: Vibrio phage KVP40

<400> SEQUENCE: 14

Met Ser Asp Leu Met Lys Ser Leu Lys Lys Ser Ser Thr Ser Gly Tyr
1               5                   10                  15

Ala Gln Val Leu Ser Glu Ser Gln Phe Met Phe Asp Lys Asp His Thr

```
            20                  25                  30
Arg Thr Tyr Val Pro Ala Ile Asn Ile Ala Phe Ser Gly Glu Val Asp
             35                  40                  45
Gly Gly Leu Thr Ser Gly Leu Thr Val Leu Ala Gly Pro Ser Lys His
 50                  55                  60
Phe Lys Ser Asn Leu Gly Leu Val Gly Val Ala Ala Tyr Leu Lys Lys
 65                  70                  75                  80
Tyr Pro Asp Ala Val Cys Val Phe Ile Asp Thr Glu Phe Gly Ile Thr
                 85                  90                  95
Pro Ser Tyr Leu Arg Ser Gln Gly Val Asp Pro Asp Arg Val Leu His
            100                 105                 110
Ile Gln Cys Glu Ser Val Glu Arg Met Lys Phe Glu Met Ala Asn Gln
            115                 120                 125
Leu Lys Asp Leu Ala Glu Arg Lys Arg Ala Lys Ala Gly Glu Glu
            130                 135                 140
Pro Asp Arg Val Ile Phe Phe Ile Asp Ser Val Gly Asn Val Ala Ser
145                 150                 155                 160
Ala Lys Glu Ile Asp Asp Ala Gln Asn Glu Lys Ser Val Ala Asp Met
                165                 170                 175
Ser Arg Ala Lys Gln Leu Lys Ser Leu Phe Arg Ile Ile Thr Pro Tyr
            180                 185                 190
Phe Thr Met Leu Asp Ile Pro Cys Ile Ala Ile Asn His Thr Tyr Gln
            195                 200                 205
Thr Gln Glu Ile Tyr Ser Lys Thr Val Met Ser Gly Thr Gly Ile
            210                 215                 220
Met Tyr Ser Ala Asp Thr Val Ile Ile Leu Gly Lys Gln Gln Glu Lys
225                 230                 235                 240
Asp Gly Lys Asp Ile Ile Gly Tyr His Phe Ile Met Asn Ile Glu Lys
                245                 250                 255
Ser Arg Phe Val Lys Glu Lys Met Lys Val Pro Leu Thr Val Thr Tyr
            260                 265                 270
Glu Asn Gly Ile Asp Pro Phe Ser Gly Leu Leu Asp Ile Ala Leu Gln
            275                 280                 285
Thr Gly His Val Val Lys Pro Ser Asn Gly Trp Tyr Gln Arg Ala Thr
            290                 295                 300
Val Asp Glu Glu Thr Gly Glu Met Ile Val Glu Glu Lys Lys Tyr Arg
305                 310                 315                 320
Ala Lys Glu Thr Gln Thr Ile Ser Phe Trp Lys Asp Ile Ile Asn Ser
                325                 330                 335
Pro Thr Phe Lys Glu Gly Val Lys Arg Ile Tyr Cys Leu Gly Gln Leu
            340                 345                 350
Asp Glu Ser Glu Leu Phe Gly Glu Val Asp Ser Leu Phe Asp
            355                 360                 365

<210> SEQ ID NO 15
<211> LENGTH: 386
<212> TYPE: PRT
<213> ORGANISM: Enterobacteria phage RB43

<400> SEQUENCE: 15

Met Ser Asn Lys Ala Leu Leu Lys Lys Leu Ile Lys Asn Ser Asn Ser
1               5                  10                  15
Gln Ser Ala Ala Ile Leu Ser Glu Ser Asp Val Phe Asn Asn Ile Thr
            20                  25                  30
```

```
Lys Thr Arg Thr Arg Val Pro Ile Leu Asn Leu Ala Leu Ser Gly Ala
         35                  40                  45

Phe Asp Gly Gly Leu Thr Ser Gly Leu Thr Leu Phe Ala Gly Pro Ser
 50                      55                  60

Lys His Phe Lys Ser Asn Leu Gly Leu Val Thr Val Ser Ala Tyr Leu
 65                  70                  75                  80

Lys Ala Asn Glu Asp Ala Val Cys Leu Phe Tyr Asp Ser Glu Lys Gly
                 85                  90                  95

Val Thr Lys Ser Tyr Leu Lys Ser Met Gly Val Asp Pro Asp Arg Val
            100                 105                 110

Val Tyr Thr Arg Ile Thr Thr Val Glu Gln Leu Arg Asn Asp Val Val
            115                 120                 125

Ser Gln Leu Asp Ala Leu Glu Arg Gly Asp Lys Val Ile Ile Phe Val
        130                 135                 140

Asp Ser Val Gly Asn Thr Ala Ser Lys Lys Glu Leu Ala Asp Ala Leu
145                 150                 155                 160

Ser Asp Asn Asp Lys Gln Asp Met Thr Arg Ala Lys Ala Leu Lys Gly
                165                 170                 175

Met Phe Arg Met Val Thr Pro Tyr Leu Ala Asp Leu Asp Ile Pro Met
            180                 185                 190

Val Cys Ile Cys His Thr Tyr Asp Thr Gln Glu Met Tyr Ser Lys Lys
            195                 200                 205

Val Ile Ser Gly Gly Thr Gly Leu Met Tyr Ser Ala Asp Thr Ala Ile
        210                 215                 220

Ile Leu Gly Lys Gln Gln Val Lys Glu Gly Thr Glu Val Val Gly Tyr
225                 230                 235                 240

Asp Phe Ile Met Asn Ile Glu Lys Ser Arg Phe Val Lys Glu Lys Ser
                245                 250                 255

Lys Phe Pro Leu His Val Thr Tyr Glu Gly Gly Ile Ser Met Tyr Ser
            260                 265                 270

Gly Leu Leu Asp Leu Ala Met Glu Met Asn Phe Val Gln Thr Pro Thr
        275                 280                 285

Lys Gly Trp Arg Gly Arg Ala Phe Leu Asn Thr Glu Thr Gly Glu Leu
290                 295                 300

Glu Leu Glu Glu Lys Lys Trp Arg Glu Ser Glu Thr Asn Ser Ile Glu
305                 310                 315                 320

Phe Trp Arg Pro Leu Phe Thr His Gln Pro Phe Leu Asp Ala Ile Gln
                325                 330                 335

Asp Lys Tyr Arg Ile Pro Asp Lys Glu Ile Thr Asp Gly Ala Ala Leu
            340                 345                 350

Glu Asp Leu Tyr Ser Thr Asp Glu Pro Glu Ser Asn Lys Ile Asp Leu
        355                 360                 365

Asp Asp Asp Ile Pro Asp Ile Gly Ile Asp Gln Asp Glu Glu Pro
370                 375                 380

Ile Met
385

<210> SEQ ID NO 16
<211> LENGTH: 335
<212> TYPE: PRT
<213> ORGANISM: Prochlorococcus phage P-SSM2

<400> SEQUENCE: 16

Met Asp Phe Leu Lys Glu Ile Val Lys Glu Ile Gly Asp Glu Tyr Thr
 1               5                  10                  15
```

Gln Val Ala Ala Asp Ile Gln Glu Asn Glu Arg Phe Ile Asp Thr Gly
            20                  25                  30

Ser Tyr Ile Phe Asn Gly Leu Val Ser Gly Ser Ile Phe Gly Gly Val
            35                  40                  45

Ser Ser Ser Arg Ile Thr Ala Ile Ala Gly Glu Ser Ser Thr Gly Lys
 50                  55                  60

Thr Tyr Phe Ser Leu Ala Val Val Lys Asn Phe Leu Asp Asn Asn Pro
 65                  70                  75                  80

Asp Gly Tyr Cys Leu Tyr Phe Asp Thr Glu Ala Ala Val Asn Lys Gly
                85                  90                  95

Leu Leu Glu Ser Arg Gly Ile Asp Met Asn Arg Leu Val Val Val Asn
            100                 105                 110

Val Val Thr Ile Glu Glu Phe Arg Ser Lys Ala Leu Arg Ala Val Asp
            115                 120                 125

Ile Tyr Leu Lys Thr Ser Glu Glu Arg Lys Pro Cys Met Phe Val
130                 135                 140

Leu Asp Ser Leu Gly Met Leu Ser Thr Glu Lys Glu Ile Arg Asp Ala
145                 150                 155                 160

Leu Asp Asp Lys Gln Val Arg Asp Met Thr Lys Ser Gln Leu Val Lys
                165                 170                 175

Gly Ala Phe Arg Met Leu Thr Leu Lys Leu Gly Gln Ala Asn Ile Pro
            180                 185                 190

Leu Ile Val Thr Asn His Thr Tyr Asp Val Ile Gly Ser Tyr Val Pro
            195                 200                 205

Thr Lys Glu Met Gly Gly Gly Ser Gly Leu Lys Tyr Ala Ala Ser Thr
            210                 215                 220

Ile Ile Tyr Leu Ser Lys Lys Glu Lys Asp Gln Lys Glu Val Ile
225                 230                 235                 240

Gly Asn Leu Ile Lys Ala Lys Thr His Lys Ser Arg Leu Ser Lys Glu
                245                 250                 255

Asn Lys Glu Val Gln Ile Arg Leu Tyr Tyr Asp Glu Arg Gly Leu Asp
            260                 265                 270

Arg Tyr Tyr Gly Leu Leu Glu Leu Gly Glu Ile Gly Gly Met Trp Lys
            275                 280                 285

Asn Val Ala Gly Arg Tyr Glu Met Asn Gly Lys Lys Ile Tyr Ala Lys
290                 295                 300

Glu Ile Leu Lys Asn Pro Thr Glu Tyr Phe Thr Asp Asp Ile Met Glu
305                 310                 315                 320

Gln Leu Asp Asn Ile Ala Lys Glu His Phe Ser Tyr Gly Thr Asn
                325                 330                 335

<210> SEQ ID NO 17
<211> LENGTH: 336
<212> TYPE: PRT
<213> ORGANISM: Prochlorococcus phage P-SSM4

<400> SEQUENCE: 17

Met Asn Phe Leu Lys Asp Ile Ala Lys Glu Ile Gly Asn Asp Tyr Ala
 1               5                   10                  15

Ser Leu Val Ser Glu Gly Val Ser Ala Gly Asp Thr Ala Gly Phe Ile
            20                  25                  30

Asp Thr Gly Ser Tyr Ile Phe Asn Ala Leu Leu Ser Gly Ser Ile Tyr
            35                  40                  45

Gly Gly Ile Pro Asn Asn Lys Ile Thr Ala Ile Ala Gly Glu Thr Ser

```
                50                  55                  60
Thr Gly Lys Thr Phe Phe Cys Leu Gly Met Val Gln His Phe Leu Glu
 65                  70                  75                  80

Ser Asn Pro Asp Ala Gly Val Ile Tyr Phe Glu Ser Glu Ser Ala Ile
                 85                  90                  95

Ser Lys Gln Met Ile Glu Asp Arg Gly Ile Asp Ser Asn Arg Met Leu
                100                 105                 110

Leu Val Pro Val Thr Thr Val Gln Glu Phe Arg Leu Gln Ala Ile Lys
                115                 120                 125

Ile Leu Asp Lys Tyr Asn Glu Gln Thr Ala Glu Glu Arg Lys Pro Leu
130                 135                 140

Met Phe Val Leu Asp Ser Leu Gly Met Leu Ser Thr Ser Lys Glu Val
145                 150                 155                 160

Glu Asp Ser Glu Ala Gly Lys Glu Thr Arg Asp Met Thr Arg Ala Gln
                165                 170                 175

Val Val Lys Ser Ile Phe Arg Val Leu Thr Leu Lys Leu Gly Lys Ala
                180                 185                 190

Asn Val Pro Leu Ile Val Thr Asn His Thr Tyr Asp Val Val Gly Ala
                195                 200                 205

Tyr Ile Pro Thr Lys Glu Met Gly Gly Ser Gly Leu Lys Tyr Ala
210                 215                 220

Ala Ser Thr Ile Val Tyr Leu Ser Lys Lys Glu Lys Asn Gly Lys
225                 230                 235                 240

Glu Val Val Gly Asn Ile Ile Lys Cys Lys Thr Ala Lys Ser Arg Leu
                245                 250                 255

Thr Lys Glu Asn Ser Asp Val Glu Thr Arg Leu Tyr Tyr Asp Arg Gly
                260                 265                 270

Leu Asp Arg Tyr Tyr Gly Leu Leu Glu Leu Gly Glu Lys His Gly Val
                275                 280                 285

Phe Ser Arg Lys Gly Asn Arg Val Val Val Gly Asp Ser Ser Val Tyr
                290                 295                 300

Pro Ser Ala Ile Leu Ala Asp Pro Asp Lys Tyr Phe Thr Glu Glu Leu
305                 310                 315                 320

Met Glu Lys Leu Asp Glu Ala Ala Lys Glu Phe Arg Tyr Gly Asn
                325                 330                 335

<210> SEQ ID NO 18
<211> LENGTH: 343
<212> TYPE: PRT
<213> ORGANISM: Synechococcus phage S-PM2

<400> SEQUENCE: 18

Met Ser Phe Leu Asp Ser Val Ile Lys Asp Ser Lys Asn Glu Tyr Ala
 1               5                  10                  15

Ala Phe Ala Ser Glu Gly Val Ala Ala Gly Asp Val Glu Ser Phe Val
                20                  25                  30

Asp Thr Gly Ser Tyr Ile Phe Asn Ala Leu Val Ser Gly Ser Ile Phe
                35                  40                  45

Gly Gly Ile Pro Ser Asn Lys Ile Thr Ala Leu Ala Gly Glu Ser Gly
 50                  55                  60

Thr Gly Lys Thr Phe Phe Cys Leu Ser Val Val Arg Asn Phe Leu Asn
 65                  70                  75                  80

Thr Asp Pro Asp Ala Gly Val Ile Tyr Phe Glu Thr Glu Ser Ala Ile
                 85                  90                  95
```

Ser Lys Gln Met Ile Glu Arg Gly Ile Asp Ser Thr Arg Met Ile
                100                 105                 110

Ile Phe Pro Val Asp Thr Ile Glu Asp Phe Arg Thr Gln Ala Val Arg
            115                 120                 125

Ile Ile Asp Lys Tyr Met Glu Gln Asn Lys Ser Glu Arg Lys Pro Leu
        130                 135                 140

Met Phe Val Leu Asp Ser Leu Gly Met Leu Ala Thr Lys Lys Glu Val
145                 150                 155                 160

Glu Asp Ala Ser Asn Asp Lys Gln Val Arg Asp Met Thr Lys Ala Gln
                165                 170                 175

Ile Val Lys Ser Ala Phe Arg Ile Leu Thr Leu Lys Met Gly Lys Ala
            180                 185                 190

Asn Ile Pro Met Leu Val Thr Asn His Thr Tyr Asp Val Val Gly Ser
        195                 200                 205

Tyr Val Pro Thr Lys Glu Met Gly Gly Ser Gly Leu Lys Tyr Ser
210                 215                 220

Ala Ser Thr Ile Val Tyr Leu Gly Lys Lys Glu Lys Asp Gly Thr
225                 230                 235                 240

Asp Leu Val Gly Asn Ile Ile Lys Cys Glu Ala Lys Lys Ser Arg Leu
                245                 250                 255

Thr Arg Glu Gly Ser Lys Val Glu Thr Arg Leu Phe Phe Asp Gln Arg
            260                 265                 270

Gly Leu Glu Arg Tyr Tyr Gly Met Leu Glu Leu Gly Glu Arg Ala Gly
        275                 280                 285

Leu Trp Lys Asn Thr Ala Gly Arg Tyr Glu Ile Asn Gly Lys Lys Val
290                 295                 300

Tyr Gly Lys Gln Ile Leu Ala Asn Pro Asp Glu Phe Phe Thr Glu Glu
305                 310                 315                 320

Ile Leu Gln Glu Leu Asp Lys Gln Ala Gln Arg Glu Phe Leu Tyr Gly
                325                 330                 335

Ala Ser Asp Asp Gly Glu Asp
            340

<210> SEQ ID NO 19
<211> LENGTH: 393
<212> TYPE: PRT
<213> ORGANISM: Enterobacteria phage RB32

<400> SEQUENCE: 19

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys His Phe Lys Ser Asn Met Ser Leu Thr Met Val Ala Ala Tyr Leu
65                  70                  75                  80

Asn Lys Tyr Pro Asp Ala Val Cys Leu Phe Tyr Asp Ser Glu Phe Gly
                85                  90                  95

Ile Thr Pro Ala Tyr Leu Arg Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Ala Ile Glu Arg Gly Glu Lys Val Ile Val Phe Ile
130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
                180                 185                 190

Val Ala Val Asn His Thr Ile Glu Thr Ile Glu Met Phe Ser Lys Thr
            195                 200                 205

Val Met Thr Gly Gly Thr Gly Val Met Tyr Ser Ala Asp Thr Val Phe
210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Phe Ile Asp Val Lys Phe Asp Gly Gly Ile Asp Pro Tyr Ser
                260                 265                 270

Gly Leu Leu Asp Met Ala Leu Glu Leu Gly Phe Val Val Lys Pro Lys
            275                 280                 285

Asn Gly Trp Tyr Ala Arg Glu Phe Leu Asp Glu Glu Thr Gly Glu Met
290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
355                 360                 365

Glu Ser Lys Ser Lys Ser Ala Ala Asp Leu Glu Leu Thr Asp Leu Glu Gln
370                 375                 380

Leu Ser Asp Met Glu Glu Phe Asn Glu
385                 390

<210> SEQ ID NO 20
<211> LENGTH: 366
<212> TYPE: PRT
<213> ORGANISM: Vibrio phage nt-1

<400> SEQUENCE: 20

Met Ser Asp Leu Leu Lys Ser Leu Lys Lys Ser Ser Thr Ser Gly Tyr
1               5                   10                  15

Ala His Val Leu Ser Glu Ser Gln Phe Met Phe Glu Lys Asp His Thr
                20                  25                  30

Arg Thr Tyr Val Pro Ala Ile Asn Ile Ala Phe Ser Gly Glu Val Asp
            35                  40                  45

Gly Gly Leu Thr Ser Gly Leu Thr Val Leu Ala Gly Pro Ser Lys His
50                  55                  60

Phe Lys Ser Asn Leu Gly Leu Val Gly Val Ala Ala Tyr Leu Lys Lys
65                  70                  75                  80

Tyr Pro Glu Ala Ile Cys Val Phe Ile Asp Thr Glu Phe Gly Ile Thr
                85                  90                  95

Pro Ser Tyr Leu Lys Ser Gln Gly Val Asp Pro Glu Arg Val Leu His

```
                    100                 105                 110
Ile Gln Cys Glu Ser Val Glu Arg Met Lys Phe Glu Met Ala Asn Gln
            115                 120                 125
Leu Lys Asp Leu Ala Glu Arg Lys Ala Lys Lys Ala Gly Glu Glu
            130                 135                 140
Pro Asp Arg Val Val Phe Phe Ile Asp Ser Val Gly Asn Val Ala Ser
145                 150                 155                 160
Ala Lys Glu Ile Asp Asp Ala Gln Asn Glu Lys Ser Val Ala Asp Met
                165                 170                 175
Ser Arg Ala Lys Gln Leu Lys Ser Leu Phe Arg Ile Ile Thr Pro Tyr
            180                 185                 190
Phe Thr Met Leu Asp Ile Pro Cys Ile Ala Ile Asn His Thr Tyr Gln
            195                 200                 205
Thr Gln Glu Met Tyr Ser Lys Thr Val Met Ser Gly Gly Thr Gly Ile
            210                 215                 220
Met Tyr Ser Ala Asp Thr Val Ile Ile Leu Gly Lys Gln Gln Glu Lys
225                 230                 235                 240
Asp Gly Lys Glu Ile Ile Gly Tyr His Phe Ile Met Asn Ile Glu Lys
                245                 250                 255
Ser Arg Phe Val Lys Glu Lys Met Lys Val Pro Leu Thr Val Thr Tyr
            260                 265                 270
Glu His Gly Ile Asp Gln Phe Ser Gly Leu Leu Asp Ile Ala Leu Gln
            275                 280                 285
Thr Gly His Val Val Lys Pro Ser Asn Gly Trp Tyr Gln Arg Ala Phe
            290                 295                 300
Ile Asp Glu Glu Thr Gly Glu Ile Glu Ile Glu Glu Lys Lys Tyr Arg
305                 310                 315                 320
Ala Lys Glu Thr Gln Thr Leu Ser Phe Trp Lys Glu Ile Ile Asn Ser
                325                 330                 335
Pro Thr Phe Lys Thr Gly Val Lys Arg Leu Tyr Cys Leu Gly Gln Leu
            340                 345                 350
Asp Glu Ser Glu Leu Leu Asp Glu Val Asp Ser Leu Phe Asp
            355                 360                 365

<210> SEQ ID NO 21
<211> LENGTH: 381
<212> TYPE: PRT
<213> ORGANISM: Enterobacteria phage RB16

<400> SEQUENCE: 21

Met Ser Asn Lys Ala Leu Leu Lys Leu Ile Lys Asn Ser Asn Ser
1               5                   10                  15
Gln Ser Ala Ser Ile Leu Ser Glu Ser Asp Val Phe Asn Asn Ile Thr
            20                  25                  30
Lys Thr Arg Thr Arg Val Pro Ile Leu Asn Leu Val Leu Ser Gly Ala
            35                  40                  45
Phe Asp Gly Gly Leu Thr Ser Gly Leu Thr Leu Ile Ala Gly Pro Ser
        50                  55                  60
Lys His Phe Lys Ser Asn Leu Gly Leu Val Ala Val Ala Ala Tyr Leu
65                  70                  75                  80
Lys Ala Asn Glu Asp Ala Val Cys Leu Phe Tyr Asp Ser Glu Lys Gly
                85                  90                  95
Val Thr Lys Ser Tyr Leu Lys Ser Met Gly Val Asp Pro Asp Arg Val
            100                 105                 110
```

Val Tyr Thr Arg Ile Thr Thr Val Glu Gln Leu Arg Asn Asp Val Val
            115                 120                 125

Ser Gln Leu Asp Ala Leu Glu Arg Gly Asp Lys Val Ile Ile Phe Val
        130                 135                 140

Asp Ser Val Gly Asn Thr Ala Ser Lys Lys Glu Leu Lys Asp Ala Leu
145                 150                 155                 160

Glu Asp Asn Asp Lys Gln Asp Met Thr Arg Ala Lys Ala Leu Lys Gly
                165                 170                 175

Met Phe Arg Met Val Thr Pro Tyr Leu Ala Asp Ile Asp Ile Pro Met
            180                 185                 190

Val Cys Ile Cys His Thr Tyr Asp Thr Gln Glu Met Tyr Ser Lys Lys
        195                 200                 205

Val Ile Ser Gly Gly Thr Gly Leu Met Tyr Ser Ala Asp Thr Ala Ile
    210                 215                 220

Ile Leu Gly Lys Gln Gln Val Lys Glu Gly Thr Glu Val Val Gly Tyr
225                 230                 235                 240

Asp Phe Ile Met Asn Val Glu Lys Ser Arg Phe Val Lys Glu Lys Ser
                245                 250                 255

Lys Phe Pro Leu His Val Thr Tyr Glu Gly Gly Ile Ser Met Phe Ser
            260                 265                 270

Gly Leu Leu Asp Leu Ala Met Glu Met Asn Phe Val Gln Thr Pro Thr
        275                 280                 285

Lys Gly Trp Arg Gly Arg Ala Phe Leu Asn Thr Glu Thr Gly Glu Leu
    290                 295                 300

Glu Leu Glu Glu Lys Lys Trp Arg Glu Ala Glu Thr Asn Cys Ile Glu
305                 310                 315                 320

Phe Trp Lys Pro Leu Phe Lys His Gln Pro Phe Ile Asp Ala Ile Gln
                325                 330                 335

Asp Lys Tyr Arg Ile Pro Asp Lys Glu Ile Thr Asp Gly Ala Ala Leu
            340                 345                 350

Glu Asp Leu Tyr Ser Asp Val Val Glu Ser Asn Lys Val Asp Phe
        355                 360                 365

Asp Asp Asp Ile Pro Asp Asp Val Asp Leu Met Glu Glu
    370                 375                 380

<210> SEQ ID NO 22
<211> LENGTH: 391
<212> TYPE: PRT
<213> ORGANISM: Enterobacteria phage T4

<400> SEQUENCE: 22

Met Ser Asp Leu Lys Ser Arg Leu Ile Lys Ala Ser Thr Ser Lys Leu
1               5                   10                  15

Thr Ala Glu Leu Thr Ala Ser Lys Phe Phe Asn Glu Lys Asp Val Val
            20                  25                  30

Arg Thr Lys Ile Pro Met Met Asn Ile Ala Leu Ser Gly Glu Ile Thr
        35                  40                  45

Gly Gly Met Gln Ser Gly Leu Leu Ile Leu Ala Gly Pro Ser Lys Ser
    50                  55                  60

Phe Lys Ser Asn Phe Gly Leu Thr Met Val Ser Ser Tyr Met Arg Gln
65                  70                  75                  80

Tyr Pro Asp Ala Val Cys Leu Phe Tyr Asp Ser Glu Phe Gly Ile Thr
                85                  90                  95

Pro Ala Tyr Leu Arg Ser Met Gly Val Asp Pro Glu Arg Val Ile His
            100                 105                 110

Thr Pro Val Gln Ser Leu Glu Gln Leu Arg Ile Asp Met Val Asn Gln
              115                 120                 125

Leu Asp Ala Ile Glu Arg Gly Glu Lys Val Val Phe Ile Asp Ser
        130                 135                 140

Leu Gly Asn Leu Ala Ser Lys Lys Glu Thr Glu Asp Ala Leu Asn Glu
145                 150                 155                 160

Lys Val Val Ser Asp Met Thr Arg Ala Lys Thr Met Lys Ser Leu Phe
                165                 170                 175

Arg Ile Val Thr Pro Tyr Phe Ser Thr Lys Asn Ile Pro Cys Ile Ala
                180                 185                 190

Ile Asn His Thr Tyr Glu Thr Gln Glu Met Phe Ser Lys Thr Val Met
            195                 200                 205

Gly Gly Gly Thr Gly Pro Met Tyr Ser Ala Asp Thr Val Phe Ile Ile
            210                 215                 220

Gly Lys Arg Gln Ile Lys Asp Gly Ser Asp Leu Gln Gly Tyr Gln Phe
225                 230                 235                 240

Val Leu Asn Val Glu Lys Ser Arg Thr Val Lys Glu Lys Ser Lys Phe
                245                 250                 255

Lys Ile Asp Val Lys Phe Asp Gly Ile Asp Pro Tyr Ser Gly Leu
                260                 265                 270

Leu Asp Met Ala Leu Glu Leu Gly Phe Val Val Lys Pro Lys Asn Gly
            275                 280                 285

Trp Tyr Ala Arg Glu Phe Leu Asp Glu Glu Thr Gly Glu Met Ile Arg
            290                 295                 300

Glu Glu Lys Ser Trp Arg Ala Lys Asp Thr Asn Cys Thr Thr Phe Trp
305                 310                 315                 320

Gly Pro Leu Phe Lys His Gln Pro Phe Arg Asp Ala Ile Lys Arg Ala
                325                 330                 335

Tyr Gln Leu Gly Ala Ile Asp Ser Asn Glu Ile Val Glu Ala Glu Val
                340                 345                 350

Asp Glu Leu Ile Asn Ser Lys Val Glu Lys Phe Lys Ser Pro Glu Ser
            355                 360                 365

Lys Ser Lys Ser Ala Ala Asp Leu Glu Thr Asp Leu Glu Gln Leu Ser
370                 375                 380

Asp Met Glu Glu Phe Asn Glu
385                 390

<210> SEQ ID NO 23
<211> LENGTH: 393
<212> TYPE: PRT
<213> ORGANISM: Enterobacteria phage T6

<400> SEQUENCE: 23

Met Ser Ile Ala Asp Leu Lys Ser Arg Leu Ile Lys Ala Ser Thr Ser
1               5                   10                  15

Lys Met Thr Ala Glu Leu Thr Ser Lys Phe Phe Asn Glu Lys Asp
                20                  25                  30

Val Ile Arg Thr Lys Ile Pro Met Leu Asn Ile Ala Ile Ser Gly Ala
                35                  40                  45

Ile Asp Gly Gly Met Gln Ser Gly Leu Thr Ile Phe Ala Gly Pro Ser
            50                  55                  60

Lys His Phe Lys Ser Asn Met Ser Leu Thr Met Val Ala Ala Tyr Leu
65                  70                  75                  80

Asn Lys Tyr Pro Asp Ala Val Cys Leu Phe Tyr Asp Ser Glu Phe Gly

```
            85                  90                  95
Ile Thr Pro Ala Tyr Leu Arg Ser Met Gly Val Asp Pro Glu Arg Val
            100                 105                 110

Ile His Thr Pro Ile Gln Ser Val Glu Gln Leu Lys Ile Asp Met Val
            115                 120                 125

Asn Gln Leu Glu Ala Ile Glu Arg Gly Glu Lys Val Ile Val Phe Ile
130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
            195                 200                 205

Val Met Thr Gly Gly Thr Gly Val Met Tyr Ser Ala Asp Thr Val Phe
        210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Lys Ile Asp Val Lys Phe Asp Gly Gly Ile Asp Pro Tyr Ser
            260                 265                 270

Gly Leu Leu Asp Met Ala Leu Glu Leu Gly Phe Val Val Lys Pro Lys
            275                 280                 285

Asn Gly Trp Tyr Ala Arg Glu Phe Leu Asp Glu Glu Thr Gly Glu Met
        290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
            355                 360                 365

Glu Ser Lys Ser Lys Ser Ala Ala Asp Leu Glu Thr Asp Leu Glu Gln
        370                 375                 380

Leu Ser Asp Met Glu Glu Phe Asn Glu
385                 390

<210> SEQ ID NO 24
<211> LENGTH: 387
<212> TYPE: PRT
<213> ORGANISM: Acinetobacter phage 133

<400> SEQUENCE: 24

Met Ser Ser Leu Lys Glu Arg Leu Ile Lys Ala Ser Thr Ser Lys Met
1               5                   10                  15

Thr Ala Glu Leu Thr Lys Ser Lys Phe Phe Asn Asp Lys Thr Val Val
            20                  25                  30

Arg Thr Arg Ile Pro Met Leu Asn Ile Ala Ile Ser Gly Ala Leu Asn
        35                  40                  45

Gly Gly Met Gln Ser Gly Leu Thr Ile Phe Ala Gly Pro Ser Lys His
    50                  55                  60
```

```
Phe Lys Ser Asn Met Gly Leu Thr Met Val Ala Ala Tyr Met Lys Ala
 65                  70                  75                  80

Phe Pro Asp Ala Val Cys Met Phe Tyr Asp Ser Glu Phe Gly Ile Thr
                 85                  90                  95

Pro Ala Tyr Leu Lys Ala Met Gly Val Asp Pro Asp Arg Val Ile His
            100                 105                 110

Thr Pro Val Gln Ser Val Glu Gln Leu Lys Ile Asp Met Thr Asn Gln
        115                 120                 125

Leu Glu Glu Val Lys Arg Gly Glu Lys Val Ile Val Phe Ile Asp Ser
130                 135                 140

Ile Gly Asn Leu Ala Ser Lys Lys Glu Thr Glu Asp Ala Leu Asn Glu
145                 150                 155                 160

Lys Thr Thr Ala Asp Met Thr Arg Ala Lys Ala Leu Lys Ser Leu Phe
                165                 170                 175

Arg Ile Val Thr Pro Tyr Phe Ser Ile Lys Asp Ile Pro Cys Val Ala
            180                 185                 190

Val Asn His Thr Leu Gln Thr Leu Glu Met Phe Ser Lys Glu Val Met
        195                 200                 205

Thr Gly Gly Thr Gly Val Met Tyr Ser Ala Asp Thr Val Phe Phe Ile
210                 215                 220

Gly Lys Arg Gln Val Lys Asp Gly Thr Glu Leu Ala Gly Tyr Glu Phe
225                 230                 235                 240

Ile Leu Lys Ala Glu Lys Ser Arg Met Val Lys Glu Lys Ser Val Phe
                245                 250                 255

Lys Ile Thr Val Lys Phe Asp Gly Gly Ile Asp Pro Tyr Ser Gly Leu
            260                 265                 270

Leu Glu Met Ala Thr Asp Leu Gly Phe Val Val Lys Pro Lys Val Gly
        275                 280                 285

Trp Tyr Lys Arg Ala Met Met Val Asp Gly Val Met Gln His Glu Glu
290                 295                 300

Lys Ser Trp Arg Ala Lys Asp Thr Asp Ser Ile Asp Phe Trp Gly Pro
305                 310                 315                 320

Leu Phe Lys His Asp Glu Phe Arg Lys Ala Ile Glu Thr Arg Tyr Gln
                325                 330                 335

Leu Gly Ser Ile Glu Ser Asp Ala Glu Val Asp Ala Glu Val Asp Ala
            340                 345                 350

Leu Ile Gly Ser Lys Thr Thr Ala Lys Ile Ser Gly Val Asn Phe Gly
        355                 360                 365

Pro Ala Glu Ser Ala Ala Asp Lys Glu Gln Gln Leu Gly Asp Phe Val
370                 375                 380

Asp Glu Asp
385

<210> SEQ ID NO 25
<211> LENGTH: 390
<212> TYPE: PRT
<213> ORGANISM: Enterobacteria phage RB69

<400> SEQUENCE: 25

Met Ser Asp Leu Lys Ser Arg Leu Ile Lys Ala Ser Thr Ser Lys Met
  1               5                  10                  15

Thr Ala Asp Leu Thr Lys Ser Lys Leu Phe Asn Asn Arg Asp Glu Val
                 20                  25                  30

Pro Thr Arg Ile Pro Met Leu Asn Ile Ala Leu Gly Gly Ala Leu Asn
             35                  40                  45
```

```
Ala Gly Leu Gln Ser Gly Leu Thr Ile Phe Ala Ala Pro Ser Lys His
    50                  55                  60

Phe Lys Thr Leu Phe Gly Leu Thr Met Val Ala Ala Tyr Met Lys Lys
 65                  70                  75                  80

Tyr Lys Asp Ala Ile Cys Leu Phe Tyr Asp Ser Glu Phe Gly Ala Ser
                 85                  90                  95

Glu Ser Tyr Phe Arg Ser Met Gly Val Asp Leu Asp Arg Val Val His
            100                 105                 110

Thr Pro Ile Gln Ser Val Glu Gln Leu Lys Val Asp Met Thr Asn Gln
            115                 120                 125

Leu Asp Ala Ile Glu Arg Gly Asp Lys Val Ile Phe Ile Asp Ser
    130                 135                 140

Ile Gly Asn Thr Ala Ser Lys Lys Glu Thr Glu Asp Ala Leu Asn Glu
145                 150                 155                 160

Lys Val Val Gly Asp Met Ser Arg Ala Lys Ala Leu Lys Ser Leu Phe
                165                 170                 175

Arg Ile Val Thr Pro Tyr Leu Thr Ile Lys Asp Ile Pro Cys Val Ala
                180                 185                 190

Ile Asn His Thr Ala Met Glu Ile Gly Gly Leu Tyr Pro Lys Glu Ile
            195                 200                 205

Met Gly Gly Gly Thr Gly Ile Leu Tyr Ser Ala Asn Thr Val Phe Phe
            210                 215                 220

Ile Ser Lys Arg Gln Val Lys Glu Gly Thr Glu Leu Thr Gly Tyr Asp
225                 230                 235                 240

Phe Thr Leu Lys Ala Glu Lys Ser Arg Thr Val Lys Glu Lys Ser Thr
                245                 250                 255

Phe Lys Ile Thr Val Asn Phe Asp Gly Gly Ile Asp Pro Phe Ser Gly
                260                 265                 270

Leu Leu Glu Met Ala Thr Glu Ile Gly Phe Val Val Lys Pro Lys Ala
            275                 280                 285

Gly Trp Tyr Ala Arg Glu Phe Leu Asp Glu Glu Thr Gly Glu Met Ile
            290                 295                 300

Arg Glu Glu Lys Ser Trp Arg Ala Lys Ala Thr Asp Cys Val Glu Phe
305                 310                 315                 320

Trp Gly Pro Leu Phe Lys His Lys Pro Phe Arg Asp Ala Ile Glu Thr
                325                 330                 335

Lys Tyr Lys Leu Gly Ala Ile Ser Ser Ile Lys Glu Val Asp Asp Ala
                340                 345                 350

Val Asn Asp Leu Ile Asn Cys Lys Ala Thr Thr Lys Val Pro Val Lys
            355                 360                 365

Thr Ser Asp Ala Pro Ser Ala Ala Asp Ile Glu Asn Asp Leu Asp Glu
            370                 375                 380

Met Glu Asp Phe Asp Glu
385                 390

<210> SEQ ID NO 26
<211> LENGTH: 411
<212> TYPE: PRT
<213> ORGANISM: Aeromonas phage Aeh1

<400> SEQUENCE: 26

Met Ala Lys Gly Ile Lys Thr Ala Lys Thr Gly Asn Leu Gly Ser Leu
 1               5                  10                  15

Met Ser Lys Leu Ala Gly Thr Ser Ser Asn Lys Met Ser Ser Val Leu
```

```
            20                  25                  30
Ala Asp Ser Lys Phe Phe Asn Asp Lys Asp Cys Val Arg Thr Arg Val
        35                  40                  45

Pro Leu Leu Asn Leu Ala Met Ser Gly Glu Leu Asp Gly Gly Leu Thr
 50                  55                  60

Pro Gly Leu Thr Val Leu Ala Gly Pro Ser Lys His Phe Lys Ser Asn
 65                  70                  75                  80

Leu Ser Leu Val Phe Val Ala Ala Tyr Leu Arg Lys Tyr Pro Asp Ala
                    85                  90                  95

Val Cys Ile Phe Phe Asp Asn Glu Phe Gly Ser Thr Pro Gly Tyr Phe
                100                 105                 110

Glu Ser Gln Gly Val Asp Ile Ser Arg Val Ile His Cys Pro Phe Lys
            115                 120                 125

Asn Ile Glu Glu Leu Lys Phe Asp Ile Val Lys Lys Leu Glu Ala Ile
        130                 135                 140

Glu Arg Gly Asp Arg Val Ile Val Phe Val Asp Ser Ile Gly Asn Ala
145                 150                 155                 160

Ala Ser Lys Lys Glu Ile Asp Asp Ala Ile Asp Glu Lys Ser Val Ser
                165                 170                 175

Asp Met Thr Arg Ala Lys Gln Ile Lys Ser Leu Thr Arg Met Met Thr
                180                 185                 190

Pro Tyr Leu Thr Val Asn Asp Ile Pro Ala Ile Met Val Ala His Thr
            195                 200                 205

Tyr Asp Thr Gln Glu Met Tyr Ser Lys Lys Val Val Ser Gly Gly Thr
210                 215                 220

Gly Ile Thr Tyr Ser Ser Asp Thr Val Ile Ile Ile Gly Arg Gln Gln
225                 230                 235                 240

Glu Lys Asp Gly Lys Glu Leu Leu Gly Tyr Asn Phe Val Leu Asn Met
                245                 250                 255

Glu Lys Ser Arg Phe Val Lys Glu Gln Ser Lys Leu Lys Leu Glu Val
                260                 265                 270

Thr Phe Gln Gly Gly Ile Asn Thr Tyr Ser Gly Met Leu Asp Ile Ala
            275                 280                 285

Leu Glu Val Gly Phe Val Val Lys Pro Ser Asn Gly Trp Phe Ser Arg
        290                 295                 300

Ala Phe Leu Asp Glu Glu Thr Gly Glu Leu Val Glu Glu Asp Arg Lys
305                 310                 315                 320

Trp Arg Arg Ala Asp Thr Asn Cys Leu Glu Phe Trp Lys Pro Met Phe
                325                 330                 335

Ala His Gln Pro Phe Lys Thr Ala Cys Ser Asp Met Phe Lys Leu Lys
                340                 345                 350

Ser Val Ala Val Lys Asp Glu Val Phe Asp Glu Val Asp Glu Leu Phe
            355                 360                 365

Ser Gly Glu Ala Glu Met Pro Val Asn Met Gly Arg Lys Leu Asp Thr
        370                 375                 380

Ala Asp Gln Glu Glu Ile Asp Gln Leu Glu Glu Val Asp Val Glu Gly
385                 390                 395                 400

Ser Asp Ser Asp Glu Leu Phe Ala Asn Leu Asp
                405                 410

<210> SEQ ID NO 27
<211> LENGTH: 368
<212> TYPE: PRT
<213> ORGANISM: Aeromonas phage 65
```

<400> SEQUENCE: 27

```
Met Ala Lys Lys Ala Lys Val Val Asn Ser Gly Asp Leu Leu Glu Arg
1               5                   10                  15

Leu Asn Gly Thr Ser Ser Asn Lys Met Ser Ala Met Leu Ala Glu Ser
            20                  25                  30

Ile Phe Phe Asn Glu Lys Asp Thr Ile Arg Thr Arg Val Pro Ile Ile
                35                  40                  45

Asn Leu Met Met Ser Gly Arg Leu Asp Gly Ile Thr Pro Gly Leu
50                  55                  60

Thr Cys Ile Ala Gly Pro Ser Lys His Phe Lys Ser Asn Leu Ser Leu
65                  70                  75                  80

Val Met Val Ser Ala Tyr Leu Arg Lys Tyr Pro Lys Ala Val Cys Leu
                85                  90                  95

Phe Phe Asp Asn Glu Phe Gly Ser Thr Pro Asp Tyr Phe Thr Ser Gln
                100                 105                 110

Gly Val Asp Ile Ser Arg Val Val His Cys Pro Phe Ile Asp Val Glu
            115                 120                 125

Glu Leu Lys Phe Asp Ile Val Lys Lys Leu Glu Ser Ile Thr Arg Gly
130                 135                 140

Asp Lys Val Ile Ile Tyr Ile Asp Ser Ile Gly Asn Val Ala Ser Lys
145                 150                 155                 160

Lys Glu Leu Gln Asp Ala Lys Asp Glu Lys Ser Ala Gln Asp Met Thr
                165                 170                 175

Arg Ala Lys Gln Ile Lys Ser Leu Phe Arg Met Val Thr Pro Tyr Leu
            180                 185                 190

Thr Val Leu Asp Ile Pro Cys Ile Ala Val Asn His Thr Tyr Glu Thr
        195                 200                 205

Gln Glu Met Phe Ser Lys Thr Val Met Ser Gly Gly Thr Gly Pro Met
210                 215                 220

Tyr Ser Ala Asp Thr Val Ile Ile Leu Gly Lys Gln Gln Asp Lys Asp
225                 230                 235                 240

Gly Lys Glu Leu Leu Gly Tyr Asn Phe Val Met Asn Ala Glu Lys Ser
                245                 250                 255

Arg Ala Ile Lys Glu Lys Ser Lys Leu Lys Leu Met Val Ser Phe Glu
            260                 265                 270

Gly Gly Ile Asn Thr Tyr Ser Gly Leu Leu Lys Ile Ala Gln Glu Leu
        275                 280                 285

Gly Phe Val Thr Lys Pro Gln Asn Ala Arg Tyr Gln Arg Asn Phe Leu
290                 295                 300

Asp Leu Glu Pro Gly Glu Met Val Ile Pro Glu Asp Glu Lys Lys Trp
305                 310                 315                 320

Thr Glu Glu Glu Ser Asp Ser Leu Glu Phe Trp Lys Pro Met Phe Ser
                325                 330                 335

His Lys Pro Phe Met Asp Ala Val Ser Asn Ala Tyr Lys Leu Lys Ala
            340                 345                 350

Val Glu Val Ser Gln Glu Val Phe Asp Glu Val Asp Gln Leu Phe Gly
        355                 360                 365
```

<210> SEQ ID NO 28
<211> LENGTH: 366
<212> TYPE: PRT
<213> ORGANISM: Vibrio phage KVP40

<400> SEQUENCE: 28

Met Ser Asp Leu Met Lys Ser Leu Lys Lys Ser Ser Thr Ser Gly Tyr
1               5                   10                  15

Ala Gln Val Leu Ser Glu Ser Gln Phe Met Phe Asp Lys Asp His Thr
            20                  25                  30

Arg Thr Tyr Val Pro Ala Ile Asn Ile Ala Phe Ser Gly Glu Val Asp
        35                  40                  45

Gly Gly Leu Thr Ser Gly Leu Thr Val Leu Ala Gly Pro Ser Lys His
50                  55                  60

Phe Lys Ser Asn Leu Gly Leu Val Gly Val Ala Ala Tyr Leu Lys Lys
65                  70                  75                  80

Tyr Pro Asp Ala Val Cys Val Phe Ile Asp Thr Glu Phe Gly Ile Thr
                85                  90                  95

Pro Ser Tyr Leu Arg Ser Gln Gly Val Asp Pro Asp Arg Val Leu His
            100                 105                 110

Ile Gln Cys Glu Ser Val Glu Arg Met Lys Phe Glu Met Ala Asn Gln
        115                 120                 125

Leu Lys Asp Leu Ala Glu Arg Lys Ala Lys Ala Gly Glu Glu
    130                 135                 140

Pro Asp Arg Val Ile Phe Phe Ile Asp Ser Val Gly Asn Val Ala Ser
145                 150                 155                 160

Ala Lys Glu Ile Asp Asp Ala Gln Asn Glu Lys Ser Val Ala Asp Met
            165                 170                 175

Ser Arg Ala Lys Gln Leu Lys Ser Leu Phe Arg Ile Ile Thr Pro Tyr
        180                 185                 190

Phe Thr Met Leu Asp Ile Pro Cys Ile Ala Ile Asn His Thr Tyr Gln
    195                 200                 205

Thr Gln Glu Ile Tyr Ser Lys Thr Val Met Ser Gly Gly Thr Gly Ile
210                 215                 220

Met Tyr Ser Ala Asp Thr Val Ile Leu Gly Lys Gln Gln Glu Lys
225                 230                 235                 240

Asp Gly Lys Asp Ile Ile Gly Tyr His Phe Ile Met Asn Ile Glu Lys
            245                 250                 255

Ser Arg Phe Val Lys Glu Lys Met Lys Val Lys Leu Thr Val Thr Tyr
        260                 265                 270

Glu Asn Gly Ile Asp Pro Phe Ser Gly Leu Leu Asp Ile Ala Leu Gln
    275                 280                 285

Thr Gly His Val Val Lys Pro Ser Asn Gly Trp Tyr Gln Arg Ala Thr
    290                 295                 300

Val Asp Glu Glu Thr Gly Glu Met Ile Val Glu Lys Lys Tyr Arg
305                 310                 315                 320

Ala Lys Glu Thr Gln Thr Ile Ser Phe Trp Lys Asp Ile Ile Asn Ser
            325                 330                 335

Pro Thr Phe Lys Glu Gly Val Lys Arg Ile Tyr Cys Leu Gly Gln Leu
        340                 345                 350

Asp Glu Ser Glu Leu Phe Gly Glu Val Asp Ser Leu Phe Asp
    355                 360                 365

<210> SEQ ID NO 29
<211> LENGTH: 386
<212> TYPE: PRT
<213> ORGANISM: Enterobacteria phage RB43

<400> SEQUENCE: 29

Met Ser Asn Lys Ala Leu Leu Lys Lys Leu Ile Lys Asn Ser Asn Ser

```
1               5                   10                  15
Gln Ser Ala Ala Ile Leu Ser Glu Ser Asp Val Phe Asn Asn Ile Thr
                20                  25                  30
Lys Thr Arg Thr Arg Val Pro Ile Leu Asn Leu Ala Leu Ser Gly Ala
            35                  40                  45
Phe Asp Gly Gly Leu Thr Ser Gly Leu Thr Leu Phe Ala Gly Pro Ser
        50                  55                  60
Lys His Phe Lys Ser Asn Leu Gly Leu Val Thr Val Ser Ala Tyr Leu
65                  70                  75                  80
Lys Ala Asn Glu Asp Ala Val Cys Leu Phe Tyr Asp Ser Glu Lys Gly
                85                  90                  95
Val Thr Lys Ser Tyr Leu Lys Ser Met Gly Val Asp Pro Asp Arg Val
            100                 105                 110
Val Tyr Thr Arg Ile Thr Thr Val Glu Gln Leu Arg Asn Asp Val Val
        115                 120                 125
Ser Gln Leu Asp Ala Leu Glu Arg Gly Asp Lys Val Ile Ile Phe Val
    130                 135                 140
Asp Ser Val Gly Asn Thr Ala Ser Lys Lys Glu Leu Ala Asp Ala Leu
145                 150                 155                 160
Ser Asp Asn Asp Lys Gln Asp Met Thr Arg Ala Lys Ala Leu Lys Gly
                165                 170                 175
Met Phe Arg Met Val Thr Pro Tyr Leu Ala Asp Leu Asp Ile Pro Met
            180                 185                 190
Val Cys Ile Cys His Thr Tyr Asp Thr Gln Glu Met Tyr Ser Lys Lys
        195                 200                 205
Val Ile Ser Gly Gly Thr Gly Leu Met Tyr Ser Ala Asp Thr Ala Ile
    210                 215                 220
Ile Leu Gly Lys Gln Gln Val Lys Glu Gly Thr Glu Val Val Gly Tyr
225                 230                 235                 240
Asp Phe Ile Met Asn Ile Glu Lys Ser Arg Phe Val Lys Glu Lys Ser
                245                 250                 255
Lys Phe Lys Leu His Val Thr Tyr Glu Gly Gly Ile Ser Met Tyr Ser
            260                 265                 270
Gly Leu Leu Asp Leu Ala Met Glu Met Asn Phe Val Gln Thr Pro Thr
        275                 280                 285
Lys Gly Trp Arg Gly Arg Ala Phe Leu Asn Thr Glu Thr Gly Glu Leu
    290                 295                 300
Glu Leu Glu Glu Lys Lys Trp Arg Glu Ser Glu Thr Asn Ser Ile Glu
305                 310                 315                 320
Phe Trp Arg Pro Leu Phe Thr His Gln Pro Phe Leu Asp Ala Ile Gln
                325                 330                 335
Asp Lys Tyr Arg Ile Pro Asp Lys Glu Ile Thr Asp Gly Ala Ala Leu
            340                 345                 350
Glu Asp Leu Tyr Ser Thr Asp Glu Pro Glu Ser Asn Lys Ile Asp Leu
        355                 360                 365
Asp Asp Asp Ile Pro Asp Asp Ile Gly Ile Asp Gln Asp Glu Glu Pro
    370                 375                 380
Ile Met
385

<210> SEQ ID NO 30
<211> LENGTH: 335
<212> TYPE: PRT
<213> ORGANISM: Prochlorococcus phage P-SSM2
```

<400> SEQUENCE: 30

| | | | | | | | | | | | | | | |
|---|---|---|---|---|---|---|---|---|---|---|---|---|---|---|
|Met|Asp|Phe|Leu|Lys|Glu|Ile|Val|Lys|Glu|Ile|Gly|Asp|Glu|Tyr|Thr|
|1| | | |5| | | | |10| | | | |15| |

Gln Val Ala Ala Asp Ile Gln Glu Asn Glu Arg Phe Ile Asp Thr Gly
    20      25      30

Ser Tyr Ile Phe Asn Gly Leu Val Ser Gly Ser Ile Phe Gly Gly Val
    35      40      45

Ser Ser Ser Arg Ile Thr Ala Ile Ala Gly Glu Ser Ser Thr Gly Lys
 50      55      60

Thr Tyr Phe Ser Leu Ala Val Val Lys Asn Phe Leu Asp Asn Asn Pro
65      70      75      80

Asp Gly Tyr Cys Leu Tyr Phe Asp Thr Glu Ala Ala Val Asn Lys Gly
    85      90      95

Leu Leu Glu Ser Arg Gly Ile Asp Met Asn Arg Leu Val Val Val Asn
    100      105      110

Val Val Thr Ile Glu Glu Phe Arg Ser Lys Ala Leu Arg Ala Val Asp
    115      120      125

Ile Tyr Leu Lys Thr Ser Glu Glu Arg Lys Pro Cys Met Phe Val
130      135      140

Leu Asp Ser Leu Gly Met Leu Ser Thr Glu Lys Glu Ile Arg Asp Ala
145      150      155      160

Leu Asp Asp Lys Gln Val Arg Asp Met Thr Lys Ser Gln Leu Val Lys
    165      170      175

Gly Ala Phe Arg Met Leu Thr Leu Lys Leu Gly Gln Ala Asn Ile Pro
    180      185      190

Leu Ile Val Thr Asn His Thr Tyr Asp Val Ile Gly Ser Tyr Val Pro
    195      200      205

Thr Lys Glu Met Gly Gly Gly Ser Gly Leu Lys Tyr Ala Ala Ser Thr
    210      215      220

Ile Ile Tyr Leu Ser Lys Lys Lys Glu Lys Asp Gln Lys Glu Val Ile
225      230      235      240

Gly Asn Leu Ile Lys Ala Lys Thr His Lys Ser Arg Leu Ser Lys Glu
    245      250      255

Asn Lys Glu Val Lys Ile Arg Leu Tyr Tyr Asp Glu Arg Gly Leu Asp
    260      265      270

Arg Tyr Tyr Gly Leu Leu Glu Leu Gly Glu Ile Gly Gly Met Trp Lys
    275      280      285

Asn Val Ala Gly Arg Tyr Glu Met Asn Gly Lys Lys Ile Tyr Ala Lys
    290      295      300

Glu Ile Leu Lys Asn Pro Thr Glu Tyr Phe Thr Asp Asp Ile Met Glu
305      310      315      320

Gln Leu Asp Asn Ile Ala Lys Glu His Phe Ser Tyr Gly Thr Asn
    325      330      335

<210> SEQ ID NO 31
<211> LENGTH: 336
<212> TYPE: PRT
<213> ORGANISM: Prochlorococcus phage P-SSM4

<400> SEQUENCE: 31

Met Asn Phe Leu Lys Asp Ile Ala Lys Glu Ile Gly Asn Asp Tyr Ala
1      5      10      15

Ser Leu Val Ser Glu Gly Val Ser Ala Gly Asp Thr Ala Gly Phe Ile
    20      25      30

-continued

```
Asp Thr Gly Ser Tyr Ile Phe Asn Ala Leu Leu Ser Gly Ser Ile Tyr
         35                  40                  45

Gly Gly Ile Pro Asn Asn Lys Ile Thr Ala Ile Ala Gly Glu Thr Ser
 50                  55                  60

Thr Gly Lys Thr Phe Phe Cys Leu Gly Met Val Gln His Phe Leu Glu
 65                  70                  75                  80

Ser Asn Pro Asp Ala Gly Val Ile Tyr Phe Glu Ser Glu Ser Ala Ile
                 85                  90                  95

Ser Lys Gln Met Ile Glu Asp Arg Gly Ile Asp Ser Asn Arg Met Leu
                100                 105                 110

Leu Val Pro Val Thr Thr Val Gln Glu Phe Arg Leu Gln Ala Ile Lys
                115                 120                 125

Ile Leu Asp Lys Tyr Asn Glu Gln Thr Ala Glu Arg Lys Pro Leu
130                 135                 140

Met Phe Val Leu Asp Ser Leu Gly Met Leu Ser Thr Ser Lys Glu Val
145                 150                 155                 160

Glu Asp Ser Glu Ala Gly Lys Glu Thr Arg Asp Met Thr Arg Ala Gln
                165                 170                 175

Val Val Lys Ser Ile Phe Arg Val Leu Thr Leu Lys Leu Gly Lys Ala
                180                 185                 190

Asn Val Pro Leu Ile Val Thr Asn His Thr Tyr Asp Val Val Gly Ala
                195                 200                 205

Tyr Ile Pro Thr Lys Glu Met Gly Gly Gly Ser Gly Leu Lys Tyr Ala
                210                 215                 220

Ala Ser Thr Ile Val Tyr Leu Ser Lys Lys Glu Lys Asn Gly Lys
225                 230                 235                 240

Glu Val Val Gly Asn Ile Ile Lys Cys Lys Thr Ala Lys Ser Arg Leu
                245                 250                 255

Thr Lys Glu Asn Ser Asp Val Lys Thr Arg Leu Tyr Tyr Asp Arg Gly
                260                 265                 270

Leu Asp Arg Tyr Tyr Gly Leu Leu Glu Leu Gly Glu Lys His Gly Val
                275                 280                 285

Phe Ser Arg Lys Gly Asn Arg Val Val Val Gly Asp Ser Ser Val Tyr
                290                 295                 300

Pro Ser Ala Ile Leu Ala Asp Pro Asp Lys Tyr Phe Thr Glu Glu Leu
305                 310                 315                 320

Met Glu Lys Leu Asp Glu Ala Ala Lys Glu Phe Arg Tyr Gly Asn
                325                 330                 335

<210> SEQ ID NO 32
<211> LENGTH: 343
<212> TYPE: PRT
<213> ORGANISM: Synechococcus phage S-PM2

<400> SEQUENCE: 32

Met Ser Phe Leu Asp Ser Val Ile Lys Asp Ser Lys Asn Glu Tyr Ala
 1               5                  10                  15

Ala Phe Ala Ser Glu Gly Val Ala Ala Gly Asp Val Glu Ser Phe Val
                 20                  25                  30

Asp Thr Gly Ser Tyr Ile Phe Asn Ala Leu Val Ser Gly Ser Ile Phe
         35                  40                  45

Gly Gly Ile Pro Ser Asn Lys Ile Thr Ala Leu Ala Gly Glu Ser Gly
 50                  55                  60

Thr Gly Lys Thr Phe Phe Cys Leu Ser Val Val Arg Asn Phe Leu Asn
```

```
                65                  70                  75                  80
Thr Asp Pro Asp Ala Gly Val Ile Tyr Phe Glu Thr Glu Ser Ala Ile
                85                  90                  95

Ser Lys Gln Met Ile Glu Ser Arg Gly Ile Asp Ser Thr Arg Met Ile
                100                 105                 110

Ile Phe Pro Val Asp Thr Ile Glu Asp Phe Arg Thr Gln Ala Val Arg
                115                 120                 125

Ile Ile Asp Lys Tyr Met Glu Gln Asn Lys Ser Glu Arg Lys Pro Leu
            130                 135                 140

Met Phe Val Leu Asp Ser Leu Gly Met Leu Ala Thr Lys Lys Glu Val
145                 150                 155                 160

Glu Asp Ala Ser Asn Asp Lys Gln Val Arg Asp Met Thr Lys Ala Gln
                165                 170                 175

Ile Val Lys Ser Ala Phe Arg Ile Leu Thr Leu Lys Met Gly Lys Ala
                180                 185                 190

Asn Ile Pro Met Leu Val Thr Asn His Thr Tyr Asp Val Val Gly Ser
            195                 200                 205

Tyr Val Pro Thr Lys Glu Met Gly Gly Gly Ser Gly Leu Lys Tyr Ser
210                 215                 220

Ala Ser Thr Ile Val Tyr Leu Gly Lys Lys Lys Glu Lys Asp Gly Thr
225                 230                 235                 240

Asp Leu Val Gly Asn Ile Ile Lys Cys Glu Ala Lys Lys Ser Arg Leu
                245                 250                 255

Thr Arg Glu Gly Ser Lys Val Lys Thr Arg Leu Phe Phe Asp Gln Arg
                260                 265                 270

Gly Leu Glu Arg Tyr Tyr Gly Met Leu Glu Leu Gly Glu Arg Ala Gly
            275                 280                 285

Leu Trp Lys Asn Thr Ala Gly Arg Tyr Glu Ile Asn Gly Lys Lys Val
290                 295                 300

Tyr Gly Lys Gln Ile Leu Ala Asn Pro Asp Glu Phe Phe Thr Glu Glu
305                 310                 315                 320

Ile Leu Gln Glu Leu Asp Lys Gln Ala Gln Arg Glu Phe Leu Tyr Gly
                325                 330                 335

Ala Ser Asp Asp Gly Glu Asp
            340

<210> SEQ ID NO 33
<211> LENGTH: 393
<212> TYPE: PRT
<213> ORGANISM: Enterobacteria phage RB32

<400> SEQUENCE: 33

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
                20                  25                  30

Val Ile Arg Thr Lys Ile Pro Met Leu Asn Ile Ala Ile Ser Gly Ala
            35                  40                  45

Ile Asp Gly Gly Met Gln Ser Gly Leu Thr Ile Phe Ala Gly Pro Ser
        50                  55                  60

Lys His Phe Lys Ser Asn Met Ser Leu Thr Met Val Ala Ala Tyr Leu
65                  70                  75                  80

Asn Lys Tyr Pro Asp Ala Val Cys Leu Phe Tyr Asp Ser Glu Phe Gly
                85                  90                  95
```

Ile Thr Pro Ala Tyr Leu Arg Ser Met Gly Val Asp Pro Glu Arg Val
                100                 105                 110

Ile His Thr Pro Ile Gln Ser Val Glu Gln Leu Lys Ile Asp Met Val
            115                 120                 125

Asn Gln Leu Glu Ala Ile Glu Arg Gly Glu Lys Val Ile Val Phe Ile
        130                 135                 140

Asp Ser Ile Gly Asn Met Ala Ser Lys Lys Glu Thr Glu Asp Ala Leu
145                 150                 155                 160

Asn Glu Lys Ser Val Ala Asp Met Thr Arg Ala Lys Ser Leu Lys Ser
                165                 170                 175

Leu Phe Arg Ile Val Thr Pro Tyr Phe Ser Ile Lys Asn Ile Pro Cys
            180                 185                 190

Val Ala Val Asn His Thr Ile Glu Thr Ile Glu Met Phe Ser Lys Thr
        195                 200                 205

Val Met Thr Gly Gly Thr Gly Val Met Tyr Ser Ala Asp Thr Val Phe
    210                 215                 220

Ile Ile Gly Lys Arg Gln Ile Lys Asp Gly Ser Asp Leu Gln Gly Tyr
225                 230                 235                 240

Gln Phe Val Leu Asn Val Glu Lys Ser Arg Thr Val Lys Glu Lys Ser
                245                 250                 255

Lys Phe Lys Ile Asp Val Lys Phe Asp Gly Ile Asp Pro Tyr Ser
            260                 265                 270

Gly Leu Leu Asp Met Ala Leu Glu Leu Gly Phe Val Val Lys Pro Lys
        275                 280                 285

Asn Gly Trp Tyr Ala Arg Glu Phe Leu Asp Glu Thr Gly Glu Met
    290                 295                 300

Ile Arg Glu Glu Lys Ser Trp Arg Ala Lys Asp Thr Asn Cys Thr Thr
305                 310                 315                 320

Phe Trp Gly Pro Leu Phe Lys His Gln Pro Phe Arg Asp Ala Ile Lys
                325                 330                 335

Arg Ala Tyr Gln Leu Gly Ala Ile Asp Ser Asn Glu Ile Val Glu Ala
            340                 345                 350

Glu Val Asp Glu Leu Ile Asn Ser Lys Val Glu Lys Phe Lys Ser Pro
        355                 360                 365

Glu Ser Lys Ser Lys Ser Ala Ala Asp Leu Thr Asp Leu Glu Gln
    370                 375                 380

Leu Ser Asp Met Glu Glu Phe Asn Glu
385                 390

<210> SEQ ID NO 34
<211> LENGTH: 366
<212> TYPE: PRT
<213> ORGANISM: Vibrio phage nt-1

<400> SEQUENCE: 34

Met Ser Asp Leu Leu Lys Ser Leu Lys Lys Ser Ser Thr Ser Gly Tyr
1               5                   10                  15

Ala His Val Leu Ser Glu Ser Gln Phe Met Phe Glu Lys Asp His Thr
                20                  25                  30

Arg Thr Tyr Val Pro Ala Ile Asn Ile Ala Phe Ser Gly Glu Val Asp
            35                  40                  45

Gly Gly Leu Thr Ser Gly Leu Thr Val Leu Ala Gly Pro Ser Lys His
        50                  55                  60

Phe Lys Ser Asn Leu Gly Leu Val Gly Val Ala Ala Tyr Leu Lys Lys
65                  70                  75                  80

Tyr Pro Glu Ala Ile Cys Val Phe Ile Asp Thr Glu Phe Gly Ile Thr
            85                  90                  95

Pro Ser Tyr Leu Lys Ser Gln Gly Val Asp Pro Glu Arg Val Leu His
                100                 105                 110

Ile Gln Cys Glu Ser Val Glu Arg Met Lys Phe Glu Met Ala Asn Gln
            115                 120                 125

Leu Lys Asp Leu Ala Glu Arg Lys Arg Ala Lys Lys Ala Gly Glu Glu
        130                 135                 140

Pro Asp Arg Val Val Phe Phe Ile Asp Ser Val Gly Asn Val Ala Ser
145                 150                 155                 160

Ala Lys Glu Ile Asp Asp Ala Gln Asn Glu Lys Ser Val Ala Asp Met
                165                 170                 175

Ser Arg Ala Lys Gln Leu Lys Ser Leu Phe Arg Ile Ile Thr Pro Tyr
            180                 185                 190

Phe Thr Met Leu Asp Ile Pro Cys Ile Ala Ile Asn His Thr Tyr Gln
            195                 200                 205

Thr Gln Glu Met Tyr Ser Lys Thr Val Met Ser Gly Gly Thr Gly Ile
        210                 215                 220

Met Tyr Ser Ala Asp Thr Val Ile Ile Leu Gly Lys Gln Gln Glu Lys
225                 230                 235                 240

Asp Gly Lys Glu Ile Ile Gly Tyr His Phe Ile Met Asn Ile Glu Lys
                245                 250                 255

Ser Arg Phe Val Lys Glu Lys Met Lys Val Lys Leu Thr Val Thr Tyr
            260                 265                 270

Glu His Gly Ile Asp Gln Phe Ser Gly Leu Leu Asp Ile Ala Leu Gln
        275                 280                 285

Thr Gly His Val Val Lys Pro Ser Asn Gly Trp Tyr Gln Arg Ala Phe
290                 295                 300

Ile Asp Glu Glu Thr Gly Glu Ile Glu Ile Glu Glu Lys Lys Tyr Arg
305                 310                 315                 320

Ala Lys Glu Thr Gln Thr Leu Ser Phe Trp Lys Ile Ile Asn Ser
            325                 330                 335

Pro Thr Phe Lys Thr Gly Val Lys Arg Leu Tyr Cys Leu Gly Gln Leu
            340                 345                 350

Asp Glu Ser Glu Leu Leu Asp Glu Val Asp Ser Leu Phe Asp
        355                 360                 365

<210> SEQ ID NO 35
<211> LENGTH: 381
<212> TYPE: PRT
<213> ORGANISM: Enterobacteria phage RB16

<400> SEQUENCE: 35

Met Ser Asn Lys Ala Leu Leu Lys Lys Leu Ile Lys Asn Ser Asn Ser
1               5                   10                  15

Gln Ser Ala Ser Ile Leu Ser Glu Ser Asp Val Phe Asn Asn Ile Thr
            20                  25                  30

Lys Thr Arg Thr Arg Val Pro Ile Leu Asn Leu Val Leu Ser Gly Ala
        35                  40                  45

Phe Asp Gly Gly Leu Thr Ser Gly Leu Thr Leu Ile Ala Gly Pro Ser
    50                  55                  60

Lys His Phe Lys Ser Asn Leu Gly Leu Val Ala Val Ala Ala Tyr Leu
65                  70                  75                  80

Lys Ala Asn Glu Asp Ala Val Cys Leu Phe Tyr Asp Ser Glu Lys Gly

-continued

```
                        85                  90                  95
Val Thr Lys Ser Tyr Leu Lys Ser Met Gly Val Asp Pro Asp Arg Val
            100                 105                 110

Val Tyr Thr Arg Ile Thr Thr Val Glu Gln Leu Arg Asn Asp Val Val
            115                 120                 125

Ser Gln Leu Asp Ala Leu Glu Arg Gly Asp Lys Val Ile Ile Phe Val
    130                 135                 140

Asp Ser Val Gly Asn Thr Ala Ser Lys Lys Glu Leu Lys Asp Ala Leu
145                 150                 155                 160

Glu Asp Asn Asp Lys Gln Asp Met Thr Arg Ala Lys Ala Leu Lys Gly
                165                 170                 175

Met Phe Arg Met Val Thr Pro Tyr Leu Ala Asp Ile Asp Ile Pro Met
            180                 185                 190

Val Cys Ile Cys His Thr Tyr Asp Thr Gln Glu Met Tyr Ser Lys Lys
            195                 200                 205

Val Ile Ser Gly Gly Thr Gly Leu Met Tyr Ser Ala Asp Thr Ala Ile
    210                 215                 220

Ile Leu Gly Lys Gln Gln Val Lys Glu Gly Thr Glu Val Val Gly Tyr
225                 230                 235                 240

Asp Phe Ile Met Asn Val Glu Lys Ser Arg Phe Val Lys Glu Lys Ser
                245                 250                 255

Lys Phe Lys Leu His Val Thr Tyr Glu Gly Gly Ile Ser Met Phe Ser
            260                 265                 270

Gly Leu Leu Asp Leu Ala Met Glu Met Asn Phe Val Gln Thr Pro Thr
            275                 280                 285

Lys Gly Trp Arg Gly Arg Ala Phe Leu Asn Thr Glu Thr Gly Glu Leu
    290                 295                 300

Glu Leu Glu Glu Lys Lys Trp Arg Glu Ala Glu Thr Asn Cys Ile Glu
305                 310                 315                 320

Phe Trp Lys Pro Leu Phe Lys His Gln Pro Phe Ile Asp Ala Ile Gln
                325                 330                 335

Asp Lys Tyr Arg Ile Pro Asp Lys Glu Ile Thr Asp Gly Ala Ala Leu
            340                 345                 350

Glu Asp Leu Tyr Ser Asp Asp Val Val Glu Ser Asn Lys Val Asp Phe
            355                 360                 365

Asp Asp Asp Ile Pro Asp Asp Val Asp Leu Met Glu Glu
    370                 375                 380
```

RECOMBINASE MUTANTS

RELATED APPLICATIONS

The present application is a divisional application of U.S. patent application Ser. No. 14/869,744, filed Sep. 29, 2015, now issued as U.S. Pat. No. 9,982,244 on May 29, 2018, which claims priority to U.S. Provisional Patent Application Ser. No. 62/057,056, filed Sep. 29, 2014, the disclosures of which are incorporated herein by reference thereto.

SEQUENCE LISTING

The present application is being filed along with a Sequence Listing in electronic format. The Sequence Listing is provided as a file entitled IP1264AUS_ST25.TXT, created May 11, 2018, which is 98 Kb in size. The information in the electronic format of the Sequence Listing is incorporated herein by reference in its entirety.

BACKGROUND

Recombinase enzymes are useful in recombinase-mediated amplification of nucleic acids. For example, recombinase enzymes can facilitate targeting of oligonucleotides to DNA targets allow replication of DNA by a polymerase. There remains a need for modified recombinases with improved properties.

BRIEF SUMMARY

Presented herein are recombinases for improved recombinase-mediated amplification of nucleic acids. The present inventors have surprisingly identified certain altered recombinases which have substantially improved characteristics in the seeding nucleic acids onto a patterned flow cell surface. In certain embodiments, the altered recombinases of improve seeding a PCR-free library, such as a PCR-library having single-stranded adapter regions, on a patterned flow cell surface for improved cluster amplification.

In certain embodiments, the recombinase is a recombinant UvsX and comprises an amino acid substitution mutation at the position functionally equivalent to Pro256 in the RB49 UvsX amino acid sequence. The wild type RB49 UvsX amino acid sequence is set forth in SEQ ID NO: 1. In certain embodiments, the recombinant UvsX comprises an amino acid sequence which comprises an amino acid that is at least 60%, 70%, 80%, 90%, 95%, 99% identical to SEQ ID NO: 1, and comprises an amino acid substitution mutation at the position functionally equivalent to Pro256 in the RB49 UvsX amino acid sequence. In certain embodiments, the substitution mutation comprises a mutation to a charged residue. In certain embodiments, the substitution mutation comprises a mutation to a basic residue. In certain embodiments, the substitution mutation comprises a mutation homologous to Pro256Lys in the RB49 UvsX amino acid sequence.

In some embodiments, in addition to the above mutations, the recombinant UvsX can further comprise substitution mutations at positions functionally equivalent to His63 in the RB49 UvsX amino acid sequence. For example, in certain embodiments, the recombinant UvsX comprises a substitution mutation homologous to His63Ser in the RB49 UvsX amino acid sequence.

In some embodiments, in addition to any of the above mutations, the recombinant UvsX can further comprise a mutation selected from the group consisting of: the addition of one or more glutamic acid residues at the C-terminus; the addition of one or more aspartic acid residues at the C-terminus; and a combination thereof.

In some embodiments, the recombinant UvsX is derived from a myoviridae phage selected from the group consisting of: T4, T6, Rb69, Aeh1, KVP40, *Acinetobacter* phage 133, *Aeromonas* phage 65, cyanophage P-SSM2, cyanophage PSSM4, cyanophage S-PM2, Rb32, *Vibrio* phage nt-1, Rb16, Rb43, and Rb49.

In some embodiments, the recombinant UvsX is derived from a myoviridae phage selected from the group consisting of: T2, Rb14, *Aeromonas* phage 25, phi-1, Phage 31, phage 44RR2.8t, phage Rb3, and phage LZ2.

Also presented herein is a recombinant UvsX comprising the amino acid sequence of any one of SEQ ID NOs: 2 and 22-35. In certain embodiments, the recombinant UvsX comprises an amino acid sequence which comprises an amino acid that is at least 60%, 70%, 80%, 90%, 95%, 99% identical to any one of SEQ ID NOs: 2 and 22-35 and which comprises an amino acid substitution mutation at the position functionally equivalent to Pro256 in the RB49 UvsX amino acid sequence.

Also presented herein is a recombinant UvsX comprising a substitution mutation to the semi-conserved domain comprising the amino acid sequence of any of SEQ ID NOs: 3-5 wherein the substitution mutation comprises a mutation selected from a substitution at position 7 to any residue other than Phe, Pro, Asp, Glu or Asn. In certain embodiments, the recombinant UvsX comprises an amino acid that is at least 60%, 70%, 80%, 90%, 95%, 99% identical to a recombinase that comprises the semi-conserved domain comprising the amino acid sequence of any of SEQ ID NOs: 3-5, and wherein the recombinant UvsX comprises a substitution mutation selected from a substitution at position 7 to any residue other than Phe, Pro, Asp, Glu or Asn. In certain embodiments, the mutation comprises a mutation to a charged residue. In certain embodiments, the mutation comprises a mutation to a basic residue. In certain embodiments, the mutation comprises a substitution at position 7 to Lys.

Also presented herein is a recombinant UvsX comprising a substitution mutation to the semi-conserved domain comprising the amino acid sequence of any of SEQ ID NOs: 6-7 wherein the substitution mutation comprises a mutation selected from a substitution at position 12 to any residue other than Phe, Pro, Asp, Glu or Asn. In certain embodiments, the recombinant UvsX comprises an amino acid that is at least 60%, 70%, 80%, 90%, 95%, 99% identical to a recombinase that comprises the semi-conserved domain comprising the amino acid sequence of any of SEQ ID NOs: 6-7, and wherein the recombinant UvsX comprises a substitution mutation selected from a substitution at position 12 to any residue other than Phe, Pro, Asp, Glu or Asn. In certain embodiments, the mutation comprises a mutation to a charged residue. In certain embodiments, the mutation comprises a mutation to a basic residue. In certain embodiments, the mutation comprises a substitution at position 12 to Lys.

In some embodiments, in addition to the above mutations, the recombinant UvsX can further comprise substitution mutations at positions functionally equivalent to His63 in the RB49 UvsX amino acid sequence. For example, in certain embodiments, the recombinant UvsX comprises a substitution mutation homologous to His63Ser in the RB49 UvsX amino acid sequence.

In some embodiments, in addition to any of the above mutations, the recombinant UvsX can further comprise a mutation selected from the group consisting of: the addition of one or more glutamic acid residues at the C-terminus; the addition of one or more aspartic acid residues at the C-terminus; and a combination thereof.

In some embodiments, the recombinant UvsX is derived from a myoviridae phage selected from the group consisting of: T4, T6, Rb69, Aeh1, KVP40, *Acinetobacter* phage 133, *Aeromonas* phage 65, cyanophage P-SSM2, cyanophage PSSM4, cyanophage S-PM2, Rb32, *Vibrio* phage nt-1, Rb16, Rb43, and Rb49.

In some embodiments, the recombinant UvsX is derived from a myoviridae phage selected from the group consisting of: T2, Rb14, *Aeromonas* phage 25, phi-1, Phage 31, phage 44RR2.8t, phage Rb3, and phage LZ2.

Also presented herein is a nucleic acid molecule encoding a recombinant UvsX as defined in any the above embodiments. Also presented herein is an expression vector comprising the nucleic acid molecule described above. Also presented herein is a host cell comprising the vector described above.

Also presented herein is a recombinase polymerase amplification process of amplification of a target nucleic acid molecule, comprising the steps of: (a) contacting the recombinant UvsX of any of the above embodiments with a first and second nucleic acid primer to form a first and second nucleoprotein primer, wherein said nucleic acid primer comprises a single stranded region at its 3' end; (b) contacting the first and the second nucleoprotein primer to said target nucleic acid molecule thereby forming a first double-stranded structure at a first portion of said first strand and forming a second double stranded structure at a second portion of said second strand such that the 3' ends of said first nucleic acid primer and said second nucleic acid primer are oriented toward one another on the same double-stranded template nucleic acid molecule; (c) extending the 3' end of said first and second nucleic acid primer with one or more polymerases and dNTPs to generate a first and second double-stranded nucleic acid and a first and second displaced strands of nucleic acid; and (d) continuing the reaction through repetition of (b) and (c) until a desired degree of amplification is reached.

In certain embodiments of the process, the target nucleic acid molecule comprises double stranded nucleic acid. In certain embodiments, the target nucleic acid molecule comprises single stranded nucleic acid. For example, in some embodiments, the target nucleic acid comprises a single stranded adaptor region. In certain embodiments, the process is performed in the presence of a recombinase loading protein. For example, the recombinase loading protein can be selected from the group consisting of T4 UvsY, *E. coli* recO, *E. coli* recR, and a combination thereof. In certain embodiments, the process is performed in the presence of a single strand stabilizing agent selected from the group consisting of gp32, *E. coli* SSB protein, T4 gp32 protein, and derivatives thereof. In certain embodiments, the process is performed in the presence of a crowding agent selected from the group comprising polyethylene glycol, polyethylene oxide, polystyrene, Ficoll, dextran, PVP, and albumin such that the crowding agent stimulates amplification.

In certain embodiments, the process is performed on an array of amplification sites. In certain embodiments, each amplification site comprises a plurality of amplification primers for amplification of the target nucleic acid. In certain embodiments, the array of amplification sites comprises an array of features on a surface. For example, the features can be non-contiguous and can be separated by interstitial regions of the surface that lack the amplification primers. In certain embodiments, the array of amplification sites comprises beads in solution or beads on a surface. In certain embodiments, the array of amplification sites comprises an emulsion. In certain embodiments, the process occurs isothermally.

Also presented herein is a kit for performing a recombinase polymerase reaction. In certain embodiments, the kit can comprise a recombinant UvsX as defined in any the above embodiments, and one or more of the following: a single stranded DNA binding protein; a DNA polymerase; dNTPs or a mixture of dNTPs and ddNTPs; a crowding agent; a buffer; a reducing agent; ATP or ATP analog; a recombinase loading protein; a first primer and optionally a second primer.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1A is a schematic showing alignment of UvsX amino acid sequences from Enterobacteria phage T4 (T4) (SEQ ID NO: 8), Enterobacteria phage T6 (T6) (SEQ ID NO: 9), *Acinetobacter* phage 133 (Phage133) (SEQ ID NO: 10), Enterobacteria phage RB69 (Rb69) (SEQ ID NO: 11), *Aeromonas* phage Aeh1 (Aeh1) (SEQ ID NO: 12), *Aeromonas* phage 65 (Ae65) (SEQ ID NO: 13), *Vibrio* phage KVP40 (Kvp40) (SEQ ID NO: 14), Enterobacteria phage RB43 (Rb43) (SEQ ID NO: 15), *Prochlorococcus* phage P-SSM2 (PSSM2) (SEQ ID NO: 16), and *Prochlorococcus* phage P-SSM4 (PSSM4) (SEQ ID NO: 17), as also set forth in the incorporated materials of US 2009/0029421. Residues that are positionally and/or functionally equivalent to Pro256 in the RB49 UvsX amino acid sequence are highlighted and indicated by a triangle symbol.

FIG. 1B is a schematic showing a continuation of the alignment set forth in FIG. 1A.

FIG. 2 is a schematic showing alignment of UvsX amino acid sequences from Enterobacteria phage RB49 (RB49) (SEQ ID NO: 1) and Enterobacteria phage T4 (T4) (SEQ ID NO: 8). Residues that are positionally and/or functionally equivalent to Pro256 in the RB49 UvsX amino acid sequence are highlighted and indicated by a triangle symbol.

DETAILED DESCRIPTION

Figure 3A:
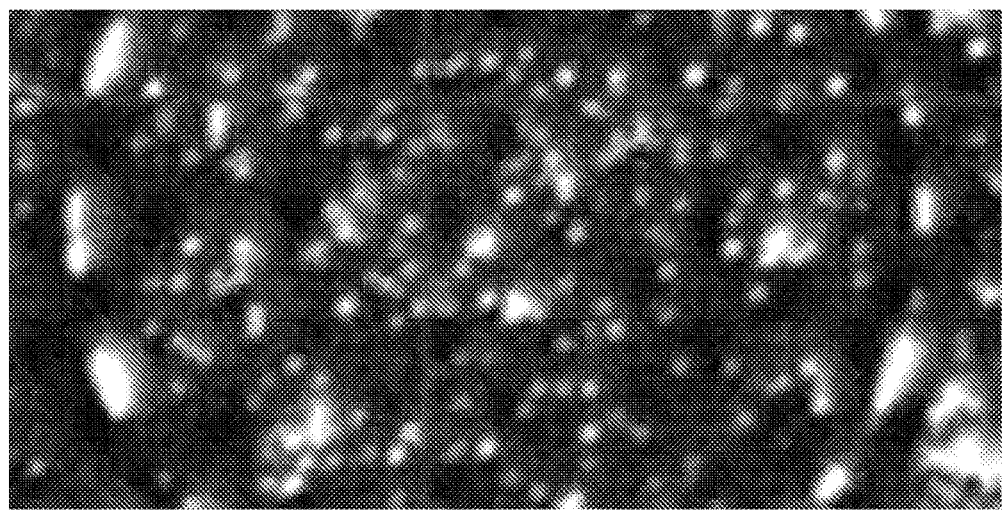
FIG. 3A shows a screenshot of a cluster image of a PCR-free library seeded onto a patterned flow cell using a T4 UvsX formulation.

Presented herein are recombinases for improved recombinase-mediated amplification of nucleic acids. The present inventors have surprisingly identified certain altered recombinases which have substantially improved characteristics in the seeding nucleic acids onto a patterned flow cell surface.

As described in greater detail hereinbelow, the inventors have surprisingly found that one or more mutations to one or more residues in the recombinase result in profound improvements in seeding a DNA library, such as, for example, a PCR-library having single-stranded adapter regions, on a patterned flow cell surface, giving improved cluster amplification.

In certain embodiments, the substitution mutation comprises a mutation to a residue having a charged side chain. For example, in some embodiments, the charged amino acid is a positively charged amino acid residue. The term "positively charged amino acid" refers to a hydrophilic amino acid with a side chain pKa value of greater than 7, namely a basic amino acid. Basic amino acids typically have positively charged side chains at physiological pH due to association with a hydronium ion. Naturally occurring (genetically encoded) basic amino acids include lysine (Lys, K), arginine (Arg, R) and histidine (His, H), while non-natural (non-genetically encoded, or non-standard) basic amino acids include, for example, ornithine, 2,3,-diaminopropionic acid, 2,4-diaminobutyric acid, 2,5,6-triaminohexanoic acid, 2-amino-4-guanidinobutanoic acid, and homoarginine. The term "negatively charged amino acid" refers to a natural or non-natural amino acid, regardless of chirality, containing, in addition to the C-terminal carboxyl group, at least one additional negatively charged group such as carboxyl, phosphate, phosphonate, sulfonate, or the like.

Also presented herein is a recombinant UvsX comprising a substitution mutation to a semi-conserved domain of the recombinant UvsX. As used herein, the term "semi-conserved domain" refers to a portion of the recombinant UvsX that is fully conserved, or at least partially conserved among various species. It has been surprisingly discovered that mutation of one or more residues in the semi-conserved domain affects the recombinase activity especially in the presence of single-strand template nucleic acid, resulting in enhancement of seeding and/or amplification in recombinase-mediated amplification reactions. These mutated recombinases have improved performance in seeding of PCR-free libraries, such as a PCR-library having single-stranded adapter regions, on a patterned flow cell surface, resulting in improved cluster amplification, as described in the Example section below.

In some embodiments, the semi-conserved domain comprises amino acids having the sequence set forth in any of SEQ ID NOs: 3-7. SEQ ID NOs: 3-7 correspond to residues in the semi-conserved domain among various species. SEQ ID NO: 3 corresponds to residues 251-258 of the T4 UvsX amino acid sequence, which is set forth herein as SEQ ID NO: 8. An alignment showing the conservation among various species in the semi-conserved domain is set forth in FIGS. 1 and 2. The UvsX sequences shown in FIG. 1 were obtained from Genbank database accession numbers NP_049656 (T4), YP_004300647 (Phage 133); NP_861734 (RB69); NP_943894.1 (Aeh1); YP_004300858 (Ae65); NP_899256 (KVP40); YP_239013 (RB43); YP_214417 (P-SSM2); YP_214708 (P-SSM4); and from US Publication No. 2009/0029421 (T6). FIG. 2 is a schematic showing alignment of UvsX amino acid sequences from Enterobacteria phage RB49 (RB49) (SEQ ID NO: 1) and Enterobacteria phage T4 (T4) (SEQ ID NO: 8). Residues that are positionally and/or functionally equivalent to Pro256 in the RB49 UvsX amino acid sequence are highlighted and indicated by a triangle. The UvsX sequences shown in FIG. 2 were obtained from Genbank database accession numbers NP_891595 (RB49) and NP_049656 (T4).

Mutations to one or more residues in the semi-conserved domain have been surprisingly found to increases the recombinase activity especially in the presence of single-strand template nucleic acid, resulting in enhancement of seeding and/or amplification in recombinase-mediated amplification reactions. These mutated recombinases have improved performance in seeding of PCR-free libraries, such as a PCR-library having single-stranded adapter regions, on a patterned flow cell surface, resulting in improved cluster amplification, as described in the Example section below. For example, in some embodiments of the recombinant UvsX presented herein, the substitution mutation comprises a mutation at position 7 of any of SEQ ID NOs: 3-5 to any residue other than other than Phe, Pro, Asp, Glu or Asn. In certain embodiments, the recombinant UvsX comprises a mutation to Lys at position 7 of any of SEQ ID NOs: 3-5. In some embodiments of the recombinant UvsX presented herein, the substitution mutation comprises a mutation at position 12 of any of SEQ ID NOs: 6-7 to any residue other than Phe, Pro, Asp, Glu or Asn. In certain embodiments, the recombinant UvsX comprises a mutation to Lys at position 12 of any of SEQ ID NOs: 6-7.

In some embodiments, the recombinase is a UvsX protein. Any phage recombinase can be used in the embodiments presented herein, including, for example phage recombinases such as UvsX or UvsX-like recombinase derived from a myoviridae phage such as, for example, T4, T6, Rb69, Aeh1, KVP40, *Acinetobacter* phage 133, *Aeromonas* phage 65, cyanophage P-SSM2, cyanophage PSSM4, cyanophage S-PM2, Rb32, *Vibrio* phage nt-1, Rb16, Rb43, and Rb49. In certain embodiments, the recombinase is a UvsX or UvsX-like recombinase derived from a myoviridae phage such as, for example, T2, Rb14, *Aeromonas* phage 25, phi-1, Phage 31, phage 44RR2.8t, phage Rb3, and phage LZ2. It will be readily apparent to one of skill in the art that other recombinase proteins can be used in the embodiments presented herein. Suitable recombinase proteins can be identified by homology to UvsX using any number of a number of methods known in the art, such as, for example, BLAST alignment, as described in greater detail below.

By "functionally equivalent" it is meant that the control recombinase, in the case of studies using a different recombinase entirely, will contain the amino acid substitution that is considered to occur at the amino acid position in the other recombinase that has the same functional role in the enzyme. As an example, the mutation at position 257 from Phenylalanine to Lysine (F257K) in the T4 UvsX would be functionally equivalent to a substitution at position 256 from Proline to Lysine (P256K) in RB49 UvsX.

Generally functionally equivalent substitution mutations in two or more different recombinases occur at homologous amino acid positions in the amino acid sequences of the recombinases. Hence, use herein of the term "functionally equivalent" also encompasses mutations that are "positionally equivalent" or "homologous" to a given mutation, regardless of whether or not the particular function of the mutated amino acid is known. It is possible to identify positionally equivalent or homologous amino acid residues in the amino acid sequences of two or more different recombinases on the basis of sequence alignment and/or molecular modelling. An example of sequence alignment to identify positionally equivalent and/or functionally equivalent residues is set forth in FIG. 1, which sets forth an alignment of UvsX amino acid sequences from Enterobacteria phage T4 (T4) (SEQ ID NO: 8), Enterobacteria phage T6 (T6) (SEQ ID NO: 9), *Acinetobacter* phage 133 (Phage133) (SEQ ID NO: 10), Enterobacteria phage RB69 (Rb69) (SEQ ID NO: 11), *Aeromonas* phage Aeh1 (Aeh1) (SEQ ID NO: 12), *Aeromonas* phage 65 (Ae65) (SEQ ID NO: 13), *Vibrio* phage KVP40 (Kvp40) (SEQ ID NO: 14), Enterobacteria phage RB43 (Rb43) (SEQ ID NO: 15),

*Prochlorococcus* phage P-SSM2 (PSSM2) (SEQ ID NO: 16), and *Prochlorococcus* phage P-SSM4 (PSSM4) (SEQ ID NO: 17), as also set forth in the incorporated materials of US 2009/0029421. The UvsX sequences shown in FIG. 1 were obtained from Genbank database accession numbers NP_049656 (T4), YP_004300647 (Phage 133); NP_861734 (RB69); NP_943894.1 (Aeh1); YP_004300858 (Ae65); NP_899256 (KVP40); YP_239013 (RB43); YP_214417 (P-SSM2); YP_214708 (P-SSM4); and from US Publication No. 2009/0029421 (T6).

FIG. 2 is a schematic showing alignment of UvsX amino acid sequences from Enterobacteria phage RB49 (RB49) (SEQ ID NO: 1) and Enterobacteria phage T4 (T4) (SEQ ID NO: 8). Residues that are positionally and/or functionally equivalent to Pro256 in the RB49 UvsX amino acid sequence are highlighted and indicated by a triangle. The UvsX sequences shown in FIG. 2 were obtained from Genbank database accession numbers NP_891595 (RB49) and NP_049656 (T4).

A positionally equivalent and/or functionally equivalent residue can be determined for one or more of any number of other UvsX sequences by aligning those sequences with that of a reference sequence such as T4 and RB49. As a non-limiting example, UvsX sequences from *Synechococcus* phage S-PM2, Enterobacteria phage RB32, *Vibrio* phage nt-1, Enterobacteria phage RB16 are set forth as SEQ ID NOs: 18-21, and obtained from Genbank database accession numbers YP_195169.1; YP_802982.1; YP_008125207.1; YP_003858336.1, can be aligned with a reference UvsX sequence such as, for example T4 UvsX (SEQ ID NO:8) and RB49 UvsX (SEQ ID NO: 1) and positionally equivalent and/or functionally equivalent residues are identified. By way of example, the residues shown in the table below are identified as positionally equivalent and/or functionally equivalent to Pro256 in the RB49 UvsX amino acid sequence. It will be readily appreciated by one of skill in the art that positionally equivalent and/or functionally equivalent positions for other UvsX proteins can be ascertained by following a similar approach.

| Phage Species | SEQ ID NO: | Positionally/Functionally Equivalent Position |
|---|---|---|
| T4 | 8 | Phe257 |
| T6 | 9 | Phe259 |
| *Acinetobacter* phage 133 | 10 | Pro257 |
| Rb69 | 11 | Pro258 |
| Aeh1 | 12 | Pro269 |
| *Aeromonas* phage 65 | 13 | Asp266 |
| KVP40 | 14 | Pro267 |
| Rb43 | 15 | Pro259 |
| cyanophage P-SSM2 | 16 | Gln261 |
| cyanophage PSSM4 | 17 | Glu264 |
| cyanophage S-PM2 | 18 | Glu264 |
| Rb32 | 19 | Phe259 |
| *Vibrio* phage nt-1 | 20 | Pro267 |
| Rb16 | 21 | Pro259 |

The recombinant UvsX proteins described hereinabove can comprise additional substitution mutations that are known to enhance one or more aspects of recombinase activity, stability or any other desirable property. For example, in some embodiments, in addition to any of the above mutations, the recombinant UvsX can further comprise substitution mutations at positions functionally equivalent His63 in the RB49 UvsX amino acid sequence as is known in the art and exemplified by the disclosure of US 2009/0029421, which is incorporated by reference in its entirety. For example, in certain embodiments, the recombinant UvsX comprises a substitution mutation homologous to His63Ser in the RB49 UvsX amino acid sequence.

In some embodiments, in addition to any of the above mutations, the recombinant UvsX can comprise additional substitution, deletion and/or addition mutations as compared to a wild type recombinase. Any of a variety of substitution mutations at one or more of positions can be made, as is known in the art and exemplified by the incorporated materials of 2009/0029421. For example, in some embodiments, in addition to the above mutations, the recombinant UvsX can further comprise a mutation selected from the group consisting of: the addition of one or more glutamic acid residues at the C-terminus; the addition of one or more aspartic acid residues at the C-terminus; and a combination thereof.

Mutating Recombinases

Various types of mutagenesis are optionally used in the present disclosure, e.g., to modify recombinases to produce variants, e.g., in accordance with recombinase models and model predictions, or using random or semi-random mutational approaches. In general, any available mutagenesis procedure can be used for making recombinase mutants. Such mutagenesis procedures optionally include selection of mutant nucleic acids and polypeptides for one or more activity of interest (e.g., enhanced seeding and/or amplification on a solid support). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting recombinase for mutation can be any of those noted herein, including available recombinases mutants such as those identified e.g., in US 2009/0029421, which is incorporated by reference in its entirety.

Optionally, mutagenesis can be guided by known information from a naturally occurring recombinase molecule, or of a known altered or mutated recombinase (e.g., using an existing mutant recombinase as noted in the preceding references), e.g., sequence, sequence comparisons, physical properties, crystal structure and/or the like as discussed above. However, in another class of embodiments, modification can be essentially random (e.g., as in classical or "family" DNA shuffling, see, e.g., Crameri et al. (1998) "DNA shuffling of a family of genes from diverse species accelerates directed evolution" Nature 391:288-291).

Additional information on mutation formats is found in: Sambrook et al., Molecular Cloning—A Laboratory Manual (3rd Ed.), Vol. 1-3, Cold Spring Harbor Laboratory, Cold Spring Harbor, N.Y., 2000 ("Sambrook"); Current Protocols in Molecular Biology, F. M. Ausubel et al., eds., Current Protocols, a joint venture between Greene Publishing Associates, Inc. and John Wiley & Sons, Inc., (supplemented through 2011) ("Ausubel")) and PCR Protocols A Guide to Methods and Applications (Innis et al. eds) Academic Press Inc. San Diego, Calif. (1990) ("Innis"). The following publications and references cited within provide additional detail on mutation formats: Arnold, Protein engineering for unusual environments, Current Opinion in Biotechnology 4:450-455 (1993); Bass et al., Mutant Trp repressors with new DNA-binding specificities, Science 242:240-245

(1988); Bordo and Argos (1991) Suggestions for "Safe" Residue Substitutions in Site-directed Mutagenesis 217:721-729; Botstein & Shortle, Strategies and applications of in vitro mutagenesis, Science 229:1193-1201 (1985); Carter et al., Improved oligonucleotide site-directed mutagenesis using M13 vectors, Nucl. Acids Res. 13: 4431-4443 (1985); Carter, Site-directed mutagenesis, Biochem. J. 237:1-7 (1986); Carter, Improved oligonucleotide-directed mutagenesis using M13 vectors, Methods in Enzymol. 154: 382-403 (1987); Dale et al., Oligonucleotide-directed random mutagenesis using the phosphorothioate method, Methods Mol. Biol. 57:369-374 (1996); Eghtedarzadeh & Henikoff, Use of oligonucleotides to generate large deletions, Nucl. Acids Res. 14: 5115 (1986); Fritz et al., Oligonucleotide-directed construction of mutations: a gapped duplex DNA procedure without enzymatic reactions in vitro, Nucl. Acids Res. 16: 6987-6999 (1988); Grundstrom et al., Oligonucleotide-directed mutagenesis by microscale 'shot-gun' gene synthesis, Nucl. Acids Res. 13: 3305-3316 (1985); Hayes (2002) Combining Computational and Experimental Screening for rapid Optimization of Protein Properties PNAS 99(25) 15926-15931; Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Point Mismatch Repair, Cell 38:879-887 (1984); Kramer et al., Improved enzymatic in vitro reactions in the gapped duplex DNA approach to oligonucleotide-directed construction of mutations, Nucl. Acids Res. 16: 7207 (1988); Ling et al., Approaches to DNA mutagenesis: an overview, Anal Biochem. 254(2): 157-178 (1997); Lorimer and Pastan Nucleic Acids Res. 23, 3067-8 (1995); Mandecki, Oligonucleotide-directed double-strand break repair in plasmids of *Escherichia coli*: a method for site-specific mutagenesis, Proc. Natl. Acad. Sci. USA, 83:7177-7181(1986); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Nambiar et al., Total synthesis and cloning of a gene coding for the ribonuclease S protein, Science 223: 1299-1301(1984); Sakamar and Khorana, Total synthesis and expression of a gene for the a-subunit of bovine rod outer segment guanine nucleotide-binding protein (transducin), Nucl. Acids Res. 14: 6361-6372 (1988); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Sieber, et al., Nature Biotechnology, 19:456-460 (2001); Smith, In vitro mutagenesis, Ann. Rev. Genet. 19:423-462 (1985); Methods in Enzymol. 100: 468-500 (1983); Methods in Enzymol. 154: 329-350 (1987); Stemmer, Nature 370, 389-91(1994); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Wells et al., Importance of hydrogen-bond formation in stabilizing the transition state of subtilisin, Phil. Trans. R. Soc. Lond. A 317: 415-423 (1986); Wells et al., Cassette mutagenesis: an efficient method for generation of multiple mutations at defined sites, Gene 34:315-323 (1985); Zoller & Smith, Oligonucleotide-directed mutagenesis using M 13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296. Additional details on many of the above methods can be found in Methods in Enzymology Volume 154, which also describes useful controls for trouble-shooting problems with various mutagenesis methods.

Making and Isolating Recombinant Recombinase

Generally, nucleic acids encoding a recombinase as presented herein can be made by cloning, recombination, in vitro synthesis, in vitro amplification and/or other available methods. A variety of recombinant methods can be used for expressing an expression vector that encodes a recombinase as presented herein. Methods for making recombinant nucleic acids, expression and isolation of expressed products are well known and described in the art. A number of exemplary mutations and combinations of mutations, as well as strategies for design of desirable mutations, are described herein.

Additional useful references for mutation, recombinant and in vitro nucleic acid manipulation methods (including cloning, expression, PCR, and the like) include Berger and Kimmel, Guide to Molecular Cloning Techniques, Methods in Enzymology volume 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and The Nucleic Acid Protocols Handbook Ralph Rapley (ed) (2000) Cold Spring Harbor, Humana Press Inc (Rapley); Chen et al. (ed) PCR Cloning Protocols, Second Edition (Methods in Molecular Biology, volume 192) Humana Press; and in Viljoen et al. (2005) Molecular Diagnostic PCR Handbook Springer, ISBN 1402034032.

In addition, a plethora of kits are commercially available for the purification of plasmids or other relevant nucleic acids from cells, (see, e.g., EasyPrep™, FlexiPrep™ both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg N.Y.) and Atlas and Parks (eds) The Handbook of Microbiological Media (1993) CRC Press, Boca Raton, Fla.

Nucleic acids encoding the recombinant recombinases of disclosed herein are also a feature of embodiments presented herein. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids presented herein are optionally "codon optimized," meaning that the nucleic acids are synthesized to include codons that are preferred by the particular translation system being employed to express the recombinase. For example, when it is desirable to express the recombinase in a bacterial cell (or even a particular strain of bacteria), the nucleic acid can be synthesized to include codons most frequently found in the genome of that bacterial cell, for efficient expression of the recombinase. A similar strategy can be employed when it is desirable to express the recombinase in a eukaryotic cell, e.g., the nucleic acid can include codons preferred by that eukaryotic cell.

A variety of protein isolation and detection methods are known and can be used to isolate recombinases, e.g., from recombinant cultures of cells expressing the recombinant recombinases presented herein. A variety of protein isolation and detection methods are well known in the art, including, e.g., those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2.sup.nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3.sup.rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ; and the references cited therein. Additional details regarding protein purification and detection methods can be found in Satinder Ahuja ed., Handbook of Bioseparations, Academic Press (2000).

Methods of Use

The altered recombinases presented herein can be used in a recombianse-mediated amplification procedure, such as a recombinase polymerase amplification (RPA) technique. Briefly, RPA can be initiated by contacting a target nucleic acid with a recombinase and a single stranded nucleic acid primer specific for the target nucleic acid molecule. The hybridized primer can then be extended by a polymerase, such as a polymerase capable of strand displacement in the presence of dNTPs to generate a double stranded target nucleic acid molecule and a displaced strand of nucleic acid molecule. Further amplification can take place by recombinase-mediated targeting of primers to the displaced strand of nucleic acid molecule and extension of the primer to generate a double stranded nucleic acid molecule. The RPA process can be modulated by combination of the above-described components with, for example, recombinase-loading factors, specific strand-displacing polymerases and a robust energy regeneration system. Exemplary RPA procedures, systems and components that can be readily adapted for use with the recombinant UvsX proteins of the present disclosure are described, for example, in U.S. Pat. Nos. 8,071,308; 7,399,590, 7,485,428, 7,270,981, 8,030,000, 7,666,598, 7,763,427, 8,017,399, 8,062,850, and 7,435,561, each of which is incorporated herein by reference.

In some embodiments, isothermal amplification can be performed using kinetic exclusion amplification (KEA), also referred to as exclusion amplification (ExAmp). A nucleic acid library of the present disclosure can be made using a method that exploits kinetic exclusion. Kinetic exclusion can occur when a process occurs at a sufficiently rapid rate to effectively exclude another event or process from occurring. Take for example the making of a nucleic acid array where sites of the array are randomly seeded with target nucleic acids from a solution and copies of the target nucleic acid are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of U.S. Application Pub. No. 2013/0338042, which is incorporated herein by reference in its entirety.

In some embodiments, the target nucleic acid that is amplified is fully double stranded. In some embodiments, the target nucleic acid that is amplified comprises a region of double stranded nucleic acid, and also comprises a region having single stranded nucleic acid. In certain embodiments, the target nucleic acid comprises one or more forked adapters with a region of about 5, 10, 15, 20, 25, 30, 35, 40 or more than about 40 bases of single stranded sequence at each end of the library fragments. Design and use of forked adapters is described in greater detail in the disclosures of U.S. Pat. Nos. 7,742,463 and 8,563,748, each of which is incorporated herein by reference in its entirety.

Kinetic exclusion can exploit a relatively slow rate for making a first copy of a target nucleic acid vs. a relatively rapid rate for making subsequent copies of the target nucleic acid or of the first copy. In the example of the previous paragraph, kinetic exclusion occurs due to the relatively slow rate of target nucleic acid seeding (e.g. relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (e.g. delayed or slow activation) vs. the relatively rapid rate at which subsequent copies are made to fill the site. In this example, an individual site may have been seeded with several different target nucleic acids (e.g. several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An amplification reagent can include further components that facilitate amplicon formation and in some cases increase the rate of amplicon formation. Recombinase, such as for example UvsX, can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590, each of which is incorporated herein by reference.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a recombinase, or the amino acid sequence of a recombinase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Nucleic Acids Encoding Altered Recombinases

Further presented herein are nucleic acid molecules encoding the altered recombinase enzymes presented herein. For any given altered recombinase which is a mutant version of a recombinase for which the amino acid sequence and preferably also the wild type nucleotide sequence encoding the recombinase is known, it is possible to obtain a nucleotide sequence encoding the mutant according to the basic principles of molecular biology. For example, given that the wild type nucleotide sequence encoding RB49 UvsX recombinase is known, it is possible to deduce a nucleotide sequence encoding any given mutant version of RB49 UvsX having one or more amino acid substitutions using the standard genetic code. Similarly, nucleotide sequences can readily be derived for mutant versions other recombinases such as, for example, T4, T6, Rb69, Aeh1, KVP40, *Acinetobacter* phage 133, *Aeromonas* phage 65, cyanophage P-SSM2, cyanophage PSSM4, cyanophage S-PM2, Rb32, *Vibrio* phage nt-1, Rb16, Rb43, T2, Rb14, *Aeromonas* phage 25, phi-1, Phage 31, phage 44RR2.8t, phage Rb3, and phage LZ2, etc. Nucleic acid molecules having the required nucleotide sequence may then be constructed using standard molecular biology techniques known in the art.

In accordance with the embodiments presented herein, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The nucleic acid molecules described herein may also, advantageously, be included in a suitable expression vector to express the recombinase proteins encoded therefrom in a suitable host. Incorporation of cloned DNA into a suitable expression vector for subsequent transformation of said cell and subsequent selection of the transformed cells is well known to those skilled in the art as provided in Sambrook et al. (1989), Molecular cloning: A Laboratory Manual, Cold Spring Harbor Laboratory, which is incorporated by reference in its entirety.

Such an expression vector includes a vector having a nucleic acid according to the embodiments presented herein operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a protein according to the embodiments presented herein.

The nucleic acid molecule may encode a mature protein or a protein having a prosequence, including that encoding a leader sequence on the preprotein which is then cleaved by the host cell to form a mature protein. The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences described by methods well known in the art.

Transcription of DNA encoding the recombinase by higher eukaryotes may be optimised by including an enhancer sequence in the vector. Enhancers are cis-acting elements of DNA that act on a promoter to increase the level of transcription. Vectors will also generally include origins of replication in addition to the selectable markers.

Example 1

This example provides methods of seeding a PCR-free library on a patterned flow cell surface for improved cluster amplification. In one embodiment, the method of the invention uses a seeding formulation that includes a UvsX comprising mutations set forth hereinabove, for example, a RB49 UvsX mutant comprising Pro256Lys (as set forth herein as SEQ ID NO: 2, referred to herein as "RB49 P256K"). It was surprisingly found that recombinase-mediated amplification using that substantially improves the seeding of PCR-libraries with single-stranded adapter regions onto a patterned flow cell surface. In another embodiment, the method of the invention uses a seeding formulation that includes a relatively high concentration of DNA polymerase (e.g., eBsu polymerase) in combination with RB49 P256K recombinase.

To evaluate the efficacy of the RB49 P256K formulation in seeding a PCR-free library onto a patterned flow cell surface, a PCR-free library was generated using a TruSeq® DNA PCR-free sample preparation kit (Illumina, Inc.). PCR-free libraries generated using the TruSeq® library preparation kit have forked adapters with a region of about 40 bases of single stranded sequence at each end of the library fragments.

Figure 3B:
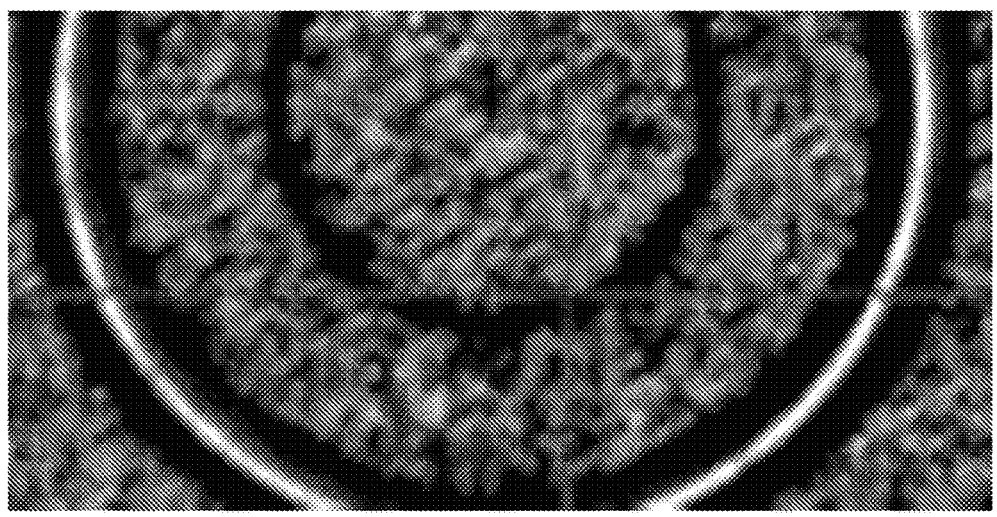
FIG. 3B shows a screenshot of a cluster image of a PCR-free library seeded onto a patterned flow cell using a liquid formulation that includes RB49 P256K recombinase.

FIG. 3A shows a screenshot 100 of a cluster image of a PCR-free library seeded onto a patterned flow cell using a standard formulation comprising T4 UvsX recombinase (as set forth herein as SEQ ID NO: 8, referred to herein as "T4 UvsX"). FIG. 3B shows a screenshot 150 of a cluster image of a PCR-free library seeded onto a patterned flow cell using a liquid formulation that includes RB49 P256K recombinase. In this example, the library was mixed with the T4 UvsX formulation or the RB49 P256K formulation to 100 pM final concentration, flushed onto a flow cell, and incubated on a cBot at 38° C. After a 1 hour incubation period, the temperature was lowered to 20° C. and the flow cell was washed with HT2 wash buffer (Illumina). Clusters were stained with a 1:5,000 dilution of SYBR® Green (Life Technologies) in 0.1 M Tris/0.1 M sodium ascorbate and imaged on a fluorescence microscope. Referring to FIG. 3A, cluster density generated by seeding a PCR-free library onto a patterned flow cell with a standard formulation (e.g., T4 UvsX) is relatively sparse. Referring to FIG. 3B, the density of clusters generated by seeding a PCR-free library onto a patterned flow cell using a formulation that includes RB49 P256K recombinase is substantially improved.

Figure 4A:
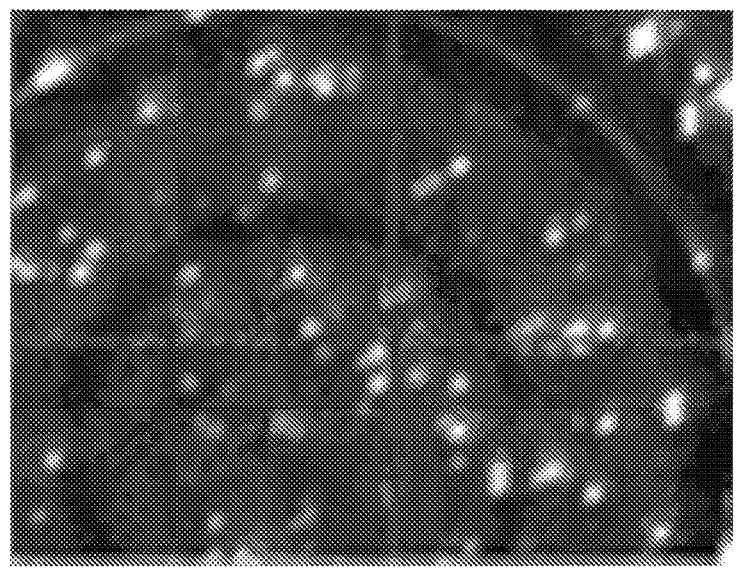
FIG. 4A shows a screenshot of a cluster image of a single stranded (ssDNA) PCR-free library seeded onto a patterned flow cell using a T4 UvsX formulation.
Figure 4B:
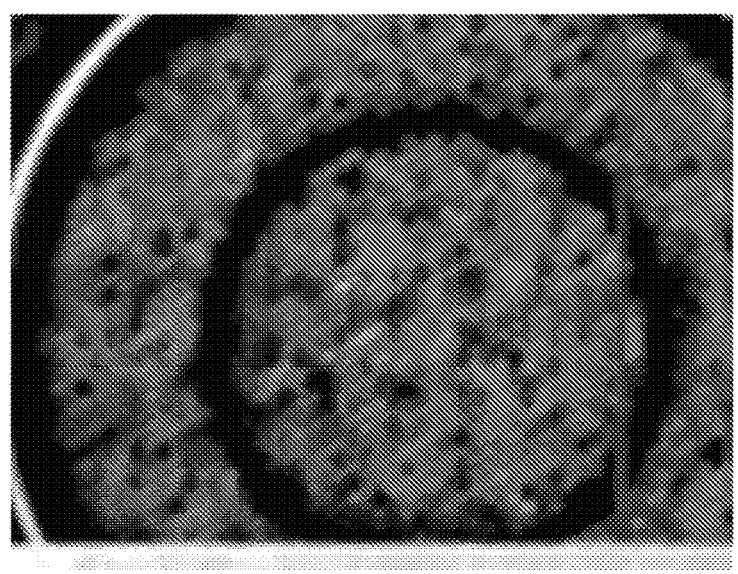
FIG. 4B shows a screenshot of a cluster image of a single stranded PCR-free library seeded onto a patterned flow cell using a liquid formulation that includes RB49 P256K recombinase.

FIG. 4A shows a screenshot 200 of a cluster image of a single stranded (ssDNA) PCR-free library seeded onto a patterned flow cell using a standard T4 UvsX formulation. FIG. 4B shows a screenshot 250 of a cluster image of a single stranded PCR-free library seeded onto a patterned flow cell using a liquid formulation that includes RB49 P256K recombinase. In this example, a double-stranded PCR-free library was denatured using NaOH and subsequently seeded onto the patterned flow cell at a concentration of 50 pM. Referring to FIG. 4A, cluster density generated by seeding a ssDNA, PCR-free DNA library onto a patterned flow cell with a standard formulation (e.g., T4 UvsX) is relatively sparse. Referring to FIG. 4B, the density of clusters generated by seeding a ssDNA PCR-free library onto a patterned flow cell using a formulation that includes RB49 P256K recombinase is substantially improved.

Example 2

Improved Amplification Using RB49 P256K Mutants

This example describes a comparison of amplification performance between recombinases with and without the P256K mutation described herein. For the purposes of this example, "control" RB49 UvsX (set forth in SEQ ID NO: 1) further comprises a H63 S mutation. A P256K mutant is generated by further mutating the control to bear a Lys residue at position 256, as set forth herein by SEQ ID NO: 2).

Clustering of a PCR-free library on a patterned flow cell is performed on a cBot as described above in Example 1, using either control or P256K mutant. Sequencing is then performed on a HiSeq instrument (Illumina, Inc.) and the sequencing results are analyzed to determine callability of a variety of regions which are typically poorly represented in previous sequencing data.

Callability is a measure of the fraction of sites at which a single nucleotide polymorphism (SNP) is called correctly. Ideally, this value is 1 (for 100%) meaning that at 100% of the sites within a particular type of region (i.e., high GC, etc) the SNPs are called correctly. Coverage is a measure of the fraction of sites which have a coverage >n, where n is typically 30× (i.e., the standard coverage for a human genome). The fosmid promoters are a set of 100 gene promoters which were identified as poorly represented in previous sequencing data. The promoters were cloned into fosmid vectors. A High GC region may be defined as a region with at least 100 bp where GC content is equal to or over 75% (N50 (G+C≥0.75) 100 N50). A Huge GC region may be defined as a region with at least 100 bp where GC content is equal to or over 85% (N50 (G+C≥0.85) 100 N50). A Low GC region may be defined as a region with at least 100 bp where GC content is equal to or less than 40% (N50 (G+C≥0.40) 100 N50). A High AT region may be defined as a region with at least 100 bp where AT content is equal to or over 75% (N50 (A+T≥0.75) 100 N50), downsampled to ~50 k regions. A Huge AT region may be defined as a region with at least 100 bp where AT content is equal to or over 85% (N50 (A+T≥0.85) 100 N50), downsampled to ~50K regions. An AT dinucleotide repeat region may be defined as a region that includes long stretches of ATAT repeats.

A comparison of callability data for control vs. P256K mutants demonstrates that the P256K mutant shows unexpected and significant improvements in callability of one or more of fosmid promoter regions, High GC, Huge GC, Low GC, High AT, Huge AT, and AT dinucleotide repeat regions, compared to that of the control.

Example 3

Improved Amplification Using Mutants Having Mutations Homologous to P256K

The performance comparison described above in Example 2 is repeated for other recombinases. In this example, "control" recombinases are generated by modifying the wild type recombinase to comprise a mutation homologous to the H63S in RB49, as set forth in the "control" column in the table below. The "P256K homolog" mutants are generated by further modifying the controls to bear a mutation homologous to the P256K in RB49 as set forth in the "P256K homolog" column in the table below.

For example, for T6 UvsX, control is generated by modifying wild type T6 UvsX (SEQ ID NO: 9) to bear a H66S mutation. The P256K homolog is further modified to bear both H66S and F259K mutations.

| WT backbone | WT backbone SEQ ID NO: | Control | P256K homolog |
|---|---|---|---|
| T4 | 8 | 64S | 64S F257K |
| T6 | 9 | H66S | H66S F259K |
| Acinetobacter phage 133 | 10 | H64S | H64S P257K |
| Rb69 | 11 | H64S | H64S P258K |
| Aeh1 | 12 | H76S | H76S P269K |
| Aeromonas phage 65 | 13 | H73S | H73S D266K |
| KVP40 | 14 | H64S | H64S P267K |
| Rb43 | 15 | H66S | H66S P259K |
| cyanophage P-SSM2 | 16 | T62S | T62S Q261K |
| cyanophage PSSM4 | 17 | T65S | T65S E264K |
| cyanophage S-PM2 | 18 | T65S | T65S E264K |
| Rb32 | 19 | H66S | H66S F259K |

-continued

| WT backbone | WT backbone SEQ ID NO: | Control | P256K homolog |
|---|---|---|---|
| Vibrio phage nt-1 | 20 | H64S | H64S P267K |
| Rb16 | 21 | H66S | H66S P259K |

Clustering of a PCR-free library on a patterned flow cell is performed on a cBot as described above in Example 1, using either control or P256K mutant. Sequencing is then performed on a HiSeq instrument (Illumina, Inc.) and the sequencing results are analyzed as described above in Example 2 to determine callability of a variety of regions which are typically poorly represented in previous sequencing data.

A comparison of callability data for control vs. P256K homolog mutants demonstrates that the P256K homolog mutants show unexpected and significant improvements in callability of one or more of fosmid promoter regions, High GC, Huge GC, Low GC, High AT, Huge AT, and AT dinucleotide repeat regions, compared to that of the control.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A UvsX recombinase polypeptide comprising an amino acid sequence that is at least 90% identical to SEQ ID NO: 11, which UvsX recombinase polypeptide comprises an amino acid substitution mutation at the position functionally equivalent to position 258 in the Enterobacteria phage RB69 UvsX of SEQ ID NO: 11, said UvsX recombinase polypeptide having increased recombinase activity compared to a T4 UvsX recombinase polypeptide having SEQ ID NO: 8 or a RB69 UvsX recombinase polypeptide having all of the amino acid sequence of SEQ ID NO: 11 except for a His to Ser substitution at amino acid position 64 of SEQ ID NO: 11.

2. The UvsX recombinase polypeptide of claim 1, wherein said substitution mutation comprises a mutation to a charged residue.

3. The UvsX recombinase polypeptide of claim 1, wherein said substitution mutation comprises a mutation to a basic residue.

4. The UvsX recombinase polypeptide of claim 3, wherein said basic residue comprises lysine (Lys), arginine (Arg), or histidine (His).

5. The UvsX recombinase polypeptide of claim 1, wherein said amino acid substitution mutation replaces the residue at the position functionally equivalent to position 258 in the polypeptide of SEQ ID NO: 11 with a lysine (Lys).

6. The UvsX recombinase polypeptide of claim 1, wherein said substitution mutation replaces the residue at the position corresponding to position 258 of the polypeptide of SEQ ID NO: 11 with any residue other than Phe, Pro, Asp, Glu or Asn.

7. The UvsX recombinase polypeptide of claim 1, wherein the UvsX recombinase polypeptide further comprises a substitution mutation at a position functionally equivalent to position 64 in the polypeptide of SEQ ID NO: 11.

8. The UvsX recombinase polypeptide of claim 7, wherein the substitution mutation replaces the residue at a position functionally equivalent to position 64 in the UvsX polypeptide of SEQ ID NO: 11 with a serine (Ser).

9. The UvsX recombinase polypeptide of claim 1, wherein said amino acid substitution mutation replaces the residue at the position functionally equivalent to position 258 of the polypeptide of SEQ ID NO: 11 with a lysine (Lys) and further comprising an amino acid substitution mutation replacing the residue at a position functionally equivalent to position 64 of the polypeptide of SEQ ID NO: 11 with serine (Ser).

10. The UvsX recombinase polypeptide of claim 1, further comprising the addition of one or more glutamic acid residues at the C-terminus, the addition of one or more aspartic acid residues at the C-terminus, or a combination thereof.

11. The UvsX recombinase polypeptide of claim 1, wherein the UvsX recombinase polypeptide comprises an amino acid sequence having at least 90% sequence identity to the amino acid sequence of SEQ ID NO: 25.

12. The UvsX recombinase polypeptide of claim 1, the UvsX recombinase polypeptide comprising an amino acid sequence that is at least 95% identical to SEQ ID NO: 11.

13. The UvsX recombinase polypeptide of claim 1, the UvsX recombinase polypeptide comprising an amino acid sequence that is at least 99% identical to SEQ ID NO: 11.

14. The UvsX recombinase polypeptide of claim 1, wherein recombinase activity is increased in the presence of a single stranded template nucleic acid compared to the T4 UvsX recombinase polypeptide having SEQ ID NO:8 or the RB69 UvsX recombinase polypeptide having all of the amino acid sequence of SEQ ID NO:11 except for a His to Ser substitution at amino acid position 64 of SEQ ID NO:11.

15. The UvsX recombinase polypeptide of claim 1, said UvsX recombinase polypeptide having improved seeding and/or amplification on a solid support compared to the T4 UvsX recombinase polypeptide having SEQ ID NO: 8 or the RB69 UvsX recombinase polypeptide having all of the amino acid sequence of SEQ ID NO: 11 except for a His to Ser substitution at amino acid position 64 of SEQ ID NO: 11.

16. The UvsX recombinase polypeptide of claim 1 comprising a semiconserved domain, said semiconserved domain comprising all of SEQ ID NO: 3, 4, or 5 except for a substitution at position 7 of SEQ ID NO: 3, 4, or 5 to any residue other than Phe, Pro, Asp, Glu or Asn, said UvsX recombinase polypeptide having increased recombinase activity compared to a T4 UvsX recombinase polypeptide having SEQ ID NO:8 or a RB69 UvsX recombinase polypeptide having all of the amino acid sequence of SEQ ID NO:11 except for a His to Ser substitution at amino acid position 64 of SEQ ID NO:11.

17. A UvsX recombinase polypeptide comprising the amino acid sequence of SEQ ID NO: 25.

18. A UvsX recombinase polypeptide comprising the amino acid sequence of SEQ ID NO:25 except for a His to Ser substitution at amino acid position 64 of SEQ ID NO:25.

* * * * *